(12) United States Patent
Riley et al.

(10) Patent No.: US 10,303,426 B2
(45) Date of Patent: May 28, 2019

(54) ATHLETIC PERFORMANCE SENSING AND/OR TRACKING SYSTEMS AND METHODS

(71) Applicant: NIKE, Inc., Beaverton, OR (US)

(72) Inventors: Raymond W. Riley, Bainbridge Island, WA (US); Kevin W. Hoffer, Beaverton, OR (US); William E. Berner, Portland, OR (US); Allan M. Schrock, Portland, OR (US); James A. Niegowski, Portland, OR (US); William F. Rauchholz, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 157 days.

(21) Appl. No.: 15/621,220

(22) Filed: Jun. 13, 2017

(65) Prior Publication Data

US 2017/0274265 A1 Sep. 28, 2017

Related U.S. Application Data

(60) Division of application No. 14/724,416, filed on May 28, 2015, now Pat. No. 9,700,780, which is a
(Continued)

(51) Int. Cl.
*G06F 3/16* (2006.01)
*G06F 16/438* (2019.01)
(Continued)

(52) U.S. Cl.
CPC ............ *G06F 3/165* (2013.01); *A61B 5/1118* (2013.01); *A61B 5/74* (2013.01); *A61B 5/7405* (2013.01);
(Continued)

(58) Field of Classification Search
None
See application file for complete search history.

(56) References Cited

U.S. PATENT DOCUMENTS

| D273,246 S | 4/1984 | Tonkel |
|---|---|---|
| 5,410,472 A | 4/1995 | Anderson |

(Continued)

FOREIGN PATENT DOCUMENTS

| CN | 1322935 A | 11/2001 |
|---|---|---|
| CN | 1621110 A | 6/2005 |

(Continued)

OTHER PUBLICATIONS

Feb. 1, 2008—(WO) Partial Search Report—App. No. PCT/US07/019384.

*Primary Examiner* — Sundhara M Ganesan
(74) *Attorney, Agent, or Firm* — Banner & Witcoff, Ltd.

(57) ABSTRACT

Athletic performance sensing and/or tracking systems include components for measuring or sensing athletic performance data and/or for storing and/or displaying desired information associated with the athletic performance to the user (or others). Such systems can allow users a wide variety of options in creating workouts, selecting and presenting media content during the athletic performance, etc., e.g., to help keep users entertained and motivated. In some instances, user feedback may be used, optionally in combination with objective data relating to a workout, to control features of the workout routine, to control the music or other media content selected and/or presented, and/or to control features of future workout routines and/or the presented media content.

7 Claims, 19 Drawing Sheets

Related U.S. Application Data continuation of application No. 14/027,616, filed on Sep. 16, 2013, now Pat. No. 9,662,560, which is a division of application No. 13/428,356, filed on Mar. 23, 2012, now Pat. No. 8,568,278, which is a continuation of application No. 12/837,893, filed on Jul. 16, 2010, now Pat. No. 8,152,695, which is a division of application No. 11/848,988, filed on Aug. 31, 2007, now Pat. No. 7,771,320.

(60) Provisional application No. 60/824,822, filed on Sep. 7, 2006.

(51) Int. Cl.

| | | |
|---|---|---|
| *G16H 20/30* | (2018.01) | |
| *A63B 24/00* | (2006.01) | |
| *G06F 19/00* | (2018.01) | |
| *A63B 71/06* | (2006.01) | |
| *G06Q 10/06* | (2012.01) | |
| *G05B 15/02* | (2006.01) | |
| *G09B 5/02* | (2006.01) | |
| *G09B 5/04* | (2006.01) | |
| *A61B 5/11* | (2006.01) | |
| *A61B 5/00* | (2006.01) | |
| *G06F 17/30* | (2006.01) | |
| *G06F 16/68* | (2019.01) | |
| *A63B 69/00* | (2006.01) | |
| *A63B 69/16* | (2006.01) | |

(52) U.S. Cl.
CPC ...... *A63B 24/0006* (2013.01); *A63B 24/0062* (2013.01); *A63B 24/0075* (2013.01); *A63B 71/06* (2013.01); *A63B 71/0616* (2013.01); *A63B 71/0622* (2013.01); *A63B 71/0686* (2013.01); *G05B 15/02* (2013.01); *G06F 16/4387* (2019.01); *G06F 17/30053* (2013.01); *G06F 19/00* (2013.01); *G06F 19/3481* (2013.01); *G06Q 10/0639* (2013.01); *G09B 5/02* (2013.01); *G09B 5/04* (2013.01); *G16H 20/30* (2018.01); *A61B 2503/10* (2013.01); *A63B 24/0059* (2013.01); *A63B 69/0028* (2013.01); *A63B 69/16* (2013.01); *A63B 2024/0065* (2013.01); *A63B 2024/0068* (2013.01); *A63B 2024/0071* (2013.01); *A63B 2071/0625* (2013.01); *A63B 2071/0694* (2013.01); *A63B 2220/00* (2013.01); *A63B 2220/12* (2013.01); *A63B 2220/17* (2013.01); *A63B 2220/20* (2013.01); *A63B 2220/30* (2013.01); *A63B 2220/836* (2013.01); *A63B 2225/20* (2013.01); *A63B 2230/06* (2013.01); *G06F 16/68* (2019.01); *G06F 17/30749* (2013.01)

(56) References Cited

U.S. PATENT DOCUMENTS

| | | | |
|---|---|---|---|
| 5,456,648 | A | 10/1995 | Edinburg et al. |
| 5,512,025 | A | 4/1996 | Dalebout et al. |
| 5,769,755 | A | 6/1998 | Henry et al. |
| 5,921,891 | A | 7/1999 | Browne |
| 6,050,924 | A | 4/2000 | Shea |
| 6,152,856 | A | 11/2000 | Studor et al. |
| 6,361,501 | B1 | 3/2002 | Amano et al. |
| 6,539,395 | B1 | 3/2003 | Gjerdingen et al. |
| 6,585,622 | B1 | 7/2003 | Shum et al. |
| 6,605,038 | B1 | 8/2003 | Teller et al. |
| 6,623,427 | B2 | 9/2003 | Mandigo |
| 6,702,719 | B1 | 3/2004 | Brown et al. |
| 6,705,672 | B2 | 3/2004 | Shikata et al. |
| 6,746,370 | B1 | 6/2004 | Fleming et al. |
| 6,808,473 | B2 | 10/2004 | Hisano et al. |
| 6,902,513 | B1 | 6/2005 | McClure |
| 7,032,178 | B1 | 4/2006 | McKnight et al. |
| 7,062,225 | B2 | 6/2006 | White |
| 7,251,454 | B2 | 7/2007 | White |
| 7,489,979 | B2 | 2/2009 | Rosenberg |
| 7,519,327 | B2 | 4/2009 | White |
| 7,521,623 | B2 | 4/2009 | Bowen |
| 7,643,895 | B2 | 1/2010 | Gupta et al. |
| 7,825,319 | B2 | 11/2010 | Turner |
| 7,867,142 | B2 | 1/2011 | Kim et al. |
| 8,568,278 | B2 | 10/2013 | Riley et al. |
| 9,643,072 | B2 | 5/2017 | Riley et al. |
| 2002/0002103 | A1 | 1/2002 | Watterson et al. |
| 2002/0002899 | A1 | 1/2002 | Gjerdingen et al. |
| 2002/0022551 | A1 | 2/2002 | Watterson et al. |
| 2002/0042328 | A1 | 4/2002 | Yoo |
| 2002/0055419 | A1 | 5/2002 | Hinnebusch |
| 2002/0093884 | A1 | 7/2002 | Hochendoner |
| 2002/0142887 | A1 | 10/2002 | O' Malley |
| 2003/0050537 | A1 | 3/2003 | Wessel |
| 2003/0171189 | A1 | 9/2003 | Kaufman |
| 2004/0043869 | A1 | 3/2004 | Sato et al. |
| 2004/0102931 | A1 | 5/2004 | Ellis et al. |
| 2004/0116088 | A1 | 6/2004 | Ellis et al. |
| 2004/0229729 | A1 | 11/2004 | Albert et al. |
| 2005/0166153 | A1 | 7/2005 | Eytchison et al. |
| 2005/0209050 | A1 | 9/2005 | Bartels |
| 2005/0215397 | A1 | 9/2005 | Watterson et al. |
| 2005/0266961 | A1 | 12/2005 | Shum et al. |
| 2006/0015193 | A1 | 1/2006 | Kato |
| 2006/0025282 | A1 | 2/2006 | Redmann |
| 2006/0063592 | A1 | 3/2006 | Teicher et al. |
| 2006/0063980 | A1 | 3/2006 | Hwang et al. |
| 2006/0084551 | A1 | 4/2006 | Volpe |
| 2006/0172859 | A1 | 8/2006 | Davis |
| 2006/0189439 | A1 | 8/2006 | Baudhuin |
| 2006/0218014 | A1 | 9/2006 | Walker et al. |
| 2006/0224451 | A1 | 10/2006 | Kerschbrock et al. |
| 2006/0240949 | A1 | 10/2006 | Wu |
| 2006/0240959 | A1 | 10/2006 | Huang |
| 2006/0252602 | A1 | 11/2006 | Brown et al. |
| 2006/0265421 | A1 | 11/2006 | Ranasinghe et al. |
| 2006/0293041 | A1 | 12/2006 | Kim |
| 2007/0040446 | A1 | 2/2007 | Hamm |
| 2007/0060446 | A1 | 3/2007 | Asukai et al. |
| 2007/0082788 | A1 | 4/2007 | Ciervo |
| 2007/0213126 | A1 | 9/2007 | Deutsch et al. |
| 2007/0219059 | A1 | 9/2007 | Schwartz et al. |
| 2007/0220552 | A1 | 9/2007 | Juster et al. |
| 2007/0225120 | A1 | 9/2007 | Schenk |
| 2007/0232455 | A1 | 10/2007 | Hanoun |
| 2007/0265138 | A1 | 11/2007 | Ashby |
| 2007/0271065 | A1 | 11/2007 | Gupta et al. |
| 2008/0103024 | A1 | 5/2008 | Habing |
| 2008/0139307 | A1 | 6/2008 | Ueshima et al. |
| 2008/0188354 | A1 | 8/2008 | Pauws et al. |
| 2008/0214358 | A1 | 9/2008 | Ogg et al. |
| 2008/0254946 | A1 | 10/2008 | Pauws et al. |

FOREIGN PATENT DOCUMENTS

| | | |
|---|---|---|
| JP | H3272786 | 12/1991 |
| JP | H1016293 A | 1/1998 |
| JP | H10230035 | 9/1998 |
| JP | 2000126334 A | 5/2000 |
| JP | 2002085618 A | 3/2002 |
| JP | 2002165769 A | 6/2002 |
| JP | 2002263213 A | 9/2002 |
| JP | 2002263232 A | 9/2002 |
| JP | 2002336209 A | 11/2002 |
| JP | 2003052648 A | 2/2003 |
| JP | 2004073460 A | 3/2004 |
| JP | 2005000636 A | 1/2005 |
| JP | 2006025282 A | 1/2006 |
| JP | 2006136717 A | 6/2006 |
| JP | 2008518127 A | 5/2008 |

(56) References Cited

FOREIGN PATENT DOCUMENTS

| WO | 02067449 A2 | 8/2002 |
|----|-------------|--------|
| WO | 2002067447 A2 | 8/2002 |
| WO | 2005082472 A1 | 9/2005 |
| WO | 2006042420 A1 | 4/2006 |
| WO | 2006065679 A2 | 6/2006 |
| WO | 2006085236 A2 | 8/2006 |

ATHLETIC PERFORMANCE SENSING AND/OR TRACKING SYSTEMS AND METHODS

RELATED APPLICATION DATA

This application is a divisional of U.S. patent application Ser. No. 14/724,416 filed May 28, 2015, which is a continuation of U.S. patent application Ser. No. 14/027,616 filed Sep. 16, 2013, which is a divisional of U.S. patent application Ser. No. 13/428,356 filed Mar. 23, 2012, which is a continuation of U.S. patent application Ser. No. 12/837,893 filed Jul. 16, 2010, which is a divisional application of U.S. patent application Ser. No. 11/848,988 filed Aug. 31, 2007 which claims priority to U.S. Provisional Patent Appln. No. 60/824,822 filed Sep. 7, 2006. The contents of the above-noted applications are incorporated herein by reference in their entirety.

Aspects of this invention relate to and/or may be used in conjunction with systems and methods of the types described, for example, in: (a) U.S. patent application Ser. No. 11/166,351 filed in the U.S. Patent and Trademark Office on Jun. 27, 2005; (b) U.S. patent application Ser. No. 11/177,489 filed Jul. 11, 2005; and (c) U.S. patent application Ser. No. 11/188,112 filed Jul. 25, 2005. Each of these applications is entirely incorporated herein by reference.

FIELD OF THE INVENTION

This invention relates generally to athletic performance sensing and/or tracking systems and methods. Such systems may include components for sensing athletic performance data and/or for storing and displaying desired information (e.g., athletic performance information) to the user. Systems in accordance with at least some aspects of this invention facilitate transfer of athletic performance data from the performance sensing system to a processing system and/or a display device, e.g., to enable data input, storage, analysis, and/or display on or by an electronic display device, including on or by conventional electronic display devices that are known and commercially available (e.g., including devices that are not typically designed and adapted for displaying athletic performance data, such as portable music and/or other audio/video display or playback devices). Systems and methods according to at least some examples of this invention allow much user control of and/or variation in entertainment, motivational, and other audio/video content presented to the user via an electronic device during an athletic performance.

BACKGROUND

Modern technology has given rise to a wide variety of different electronic and/or communication devices that keep users in touch with one another, entertained, and informed. A wide variety of portable electronic devices are available for these purposes, such as: cellular telephones; personal digital assistants ("PDAs"); pagers; beepers; MP3 or other audio playback devices; radios; portable televisions, DVD players, or other video playing devices; watches; GPS systems; etc. Many people like to carry one or more of these types of devices with them when they exercise and/or participate in athletic events, for example, to keep them in contact with others (e.g., in case of inclement weather, injuries; or emergencies; to contact coaches or trainers; etc.), to keep them entertained, to provide information (e.g., time, direction, location, etc.), and the like.

Athletic performance monitoring systems also have benefited from recent advancements in electronic device and digital technology. Electronic performance monitoring devices enable easy and convenient monitoring of many physical or physiological characteristics associated with exercise or other athletic performances, including, for example: speed and distance data, altitude data, GPS data, heart rate, pulse rate, blood pressure data, body temperature, etc. Such systems, however, have deficiencies, for example, in their portability, convenience, customizability, and/or user friendliness.

SUMMARY

Aspects of this invention relate to athletic performance sensing and/or tracking systems and/or methods. Such systems and methods may include components for measuring or sensing athletic performance data and/or for storing and/or displaying desired information associated with the athletic performance to the user (or others). More specific examples of systems and methods according to at least some examples of this invention may perform one or more of the following functions: sense one or more physical or physiological parameters associated with an athletic performance; store information regarding athletic performances; present music or other media content to users during an athletic performance; allow users to create and/or download workout routines, optionally including music or other media content for presentation during the workout routine; allow users to store information regarding the content of individual workout routines and/or individual workout activities; receive user input ranking the workout difficulty or intensity; receive user input ranking music or other media content included in or associated with a workout routine; correlate user ranking information relating to music or other media content to objective data relating to user performance during the workout routine at the time the content was presented; modify workout routines based on a user's subjective input and/or objective data relating to media content and/or user performance during presentation of specific media content; provide rewards and/or enhanced feature sets for certain, limited numbers of or specific users; determine cadence of a user's performance associated with various workout activities; compare a user's workout characteristics to other users, celebrities, athletes, etc.; participate in virtual races, competitions, and/or events (e.g., for charity, in competition with friends, etc.); provide motivational and/or reward content, optionally media content at preselected times during a workout and/or during predetermined events (e.g., when a user approaches or reaches a goal, a personal best, etc.); provide specialized workout routines based on user selected events, properties, goals, etc.; and modify and extend workout routines by adding one or more songs or additional media content to the workout routine. Systems and methods according to this invention may perform additional functions and/or use any or all of the above functions in any desired combinations or subcombinations.

Additional aspects of this invention relate to user interfaces for operating athletic performance sensing and/or tracking systems and performing athletic performance sensing and/or tracking methods (such as operating systems and/or performing methods of the types described above). Such user interfaces may be presented on a display device, such as a display device of a computer and/or a display device of a portable electronic device, e.g., a device carried by the user during the athletic performance. User interfaces according to at least some examples of this invention may use common interface interaction elements, features, and/or functions, such as elements, features, and/or functions found in commercially available user interfaces for computers and/or electronic devices, such as elements, features, and/or functions found in the graphical user interfaces for WINDOWS® based computer systems (available from Microsoft Corporation of Redmond, Wash.), MACINTOSH® based computer systems (available from Apple Computer, Inc. of Cupertino, Calif.), etc.; elements, features, and/or functions found in graphical user interfaces for commercially available cellular telephones, personal digital assistances, and/or electronic audio/video playback devices, such as IPOD® systems (available from Apple Computer, Inc. of Cupertino, Calif.).

BRIEF DESCRIPTION OF THE DRAWINGS

A more complete understanding of the present invention and at least some features and advantages thereof may be acquired by referring to the following description and the accompanying drawings, in which like reference numbers indicate like features throughout, and wherein.

DETAILED DESCRIPTION

Figure 1:
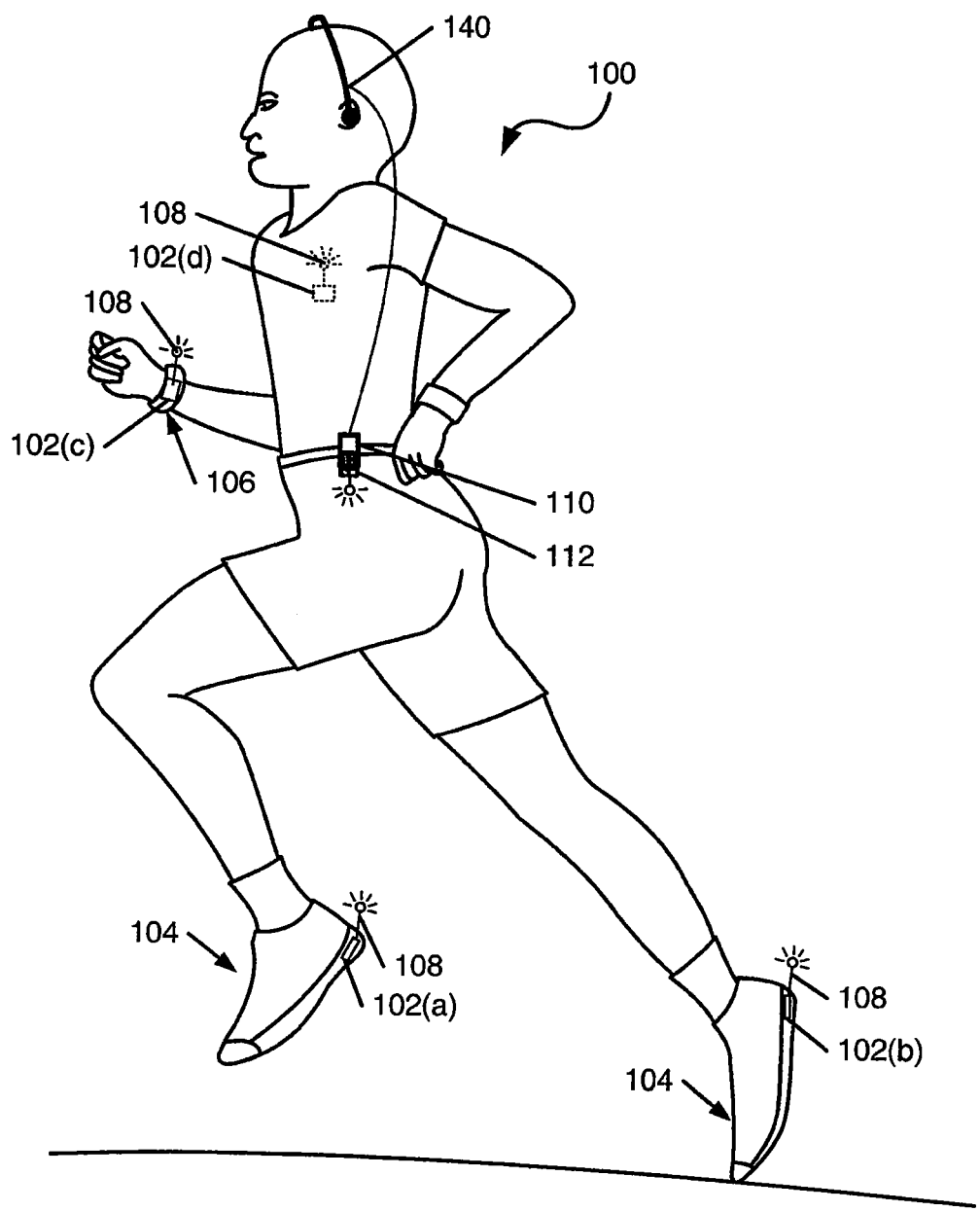
FIG. 1 illustrates example systems and an example environment in which various aspects and features of the invention may be practiced or used.

In the following description of various examples of the present invention, reference is made to the accompanying drawings, which form a part hereof, and in which are shown by way of illustration various structures, embodiments, and examples in which aspects of the invention may be used and practiced. It is to be understood that other embodiments may be utilized and structural and functional modifications may be made to the various illustrated and described elements or steps without departing from the scope of the present invention. Aspects of this invention relate to any of the components, features, elements, or steps described as part of the systems, methods, and user interfaces below, as well as to any desired combinations or subcombinations of such components, features, elements, or steps.

I. General Description of Systems Useful for Practicing Aspects of the Invention Aspects of the present invention relate generally to systems and devices used for athletic performance sensing, e.g., to measure, process, store, and/or output physical and/or physiological data associated with an athletic event, an exercise routine, or other physical or athletic performance (the terms "athletic performance" and "workout routine" are used in this specification to generically refer to any type of athletic event, exercise, training, routine, or the like, including events performed as training exercises, events performed as part of actual competitions, etc.). Some more specific aspects of this invention relate to systems and methods for providing athletic performance data to electronic devices, to enable display, further processing, output, and/or storage of the athletic performance information and/or data. In accordance with at least some examples of this invention, the electronic output device may be (and/or may include at least some functions of) a conventional and commercially available electronic audio, video, and/or alphanumeric display or output device (such as a cellular telephone, watch, PDA, pager, MP3 player, audio player, radio, portable television, portable DVD player, video playing device, or the like). At least some examples of systems and methods according to this invention may include or utilize an "adapter" or other interface system or device: (a) for receiving data from an athletic performance sensing system and (b) for transmitting data to the output device, optionally with some intervening data processing to place the data in a desired form or format, e.g., for immediate output on the output device, for storage, for retransmission, etc. The interface system or device, when present and/or necessary, may physically plug into an existing port or jack (such as a universal serial bus port, a serial port, a parallel port, or other data or power/recharger input port) provided in the output device, including into conventional ports known and used in commercially available electronic devices. This optional feature has advantages in that it provides owners of conventional electronic devices (e.g., of the types described above) the ability to display, store, output, and/or retransmit physical or physiological data collected during an athletic performance (e.g., during walking, running, biking, rowing, etc., a user could view performance data (e.g., speed, distance, heart rate, etc.) on an MP3 audio playback device display or other electronic device display and/or receive audio information via headphones connected to the MP3 player or other device with audio capabilities, or the like). If desired, the electronic device may be capable of receiving and/or processing the performance data directly, in which case the interface device may be omitted.

More specific examples of some aspects of the invention follow.

A. Receipt of Subjective User Input to Control Workout Parameters

Aspects of this invention relate to athletic performance tracking and/or control systems, methods, and computer interfaces. Such systems may include, for example: (a) a display system that presents workout information to a user (e.g., a display screen, an audio/video output system, etc.), wherein the workout information includes information relating to content of a user's workout routine; (b) a user interface system that prompts the user for a first input relating to a desired workout intensity parameter for the workout routine, wherein the user interface system prompts the user for the first input after the workout routine has begun; (c) an input system for receiving the first input; and (d) a processing system programmed and adapted to perform at least one function selected from the group of: (i) evaluating the workout routine in view of the first input, (ii) providing a revised workout routine based at least in part on the first input, and/or (iii) modifying at least one parameter of the workout routine based on the first input. Some portions or all of these functions, if desired, may be performed in and/or provided by small, handheld or other portable electronic devices, e.g., devices that may be carried by users during the course of the workout routine.

Tracking and/or control systems in accordance with at least some examples of this invention further may include one or more sensors that sense physical or physiological characteristics relating to user participation in the workout routine. The sensor(s) may sense one or more physical or physiological characteristics associated with an athletic performance, e.g., characteristics of the types described in more detail below. The athletic performance data presented by the display system may include information based on output from the sensor (such as speed information, distance information, timing information, heart rate, pulse rate, etc.).

The user interface system may prompt the user for the first input at any desired time during an athletic performance. For example, the user interface system may prompt the user for the first input (e.g., requesting an indication of the desired workout intensity level) during an initial workout activity of an overall workout routine (e.g., during an initial warm-up time period, within a first 5 to 10% of the overall workout routine time period, within a first 5 to 10% of an individual workout activity within the overall workout routine, etc.). As another example, the user interface system may prompt the user for the first input toward the end of a workout activity included in the workout routine and/or toward the end of the overall workout routine (e.g., if a user's workout results up to that time have placed the user in a position at which they may achieve a personal best, achieve a goal or milestone level, etc.; toward the end of a warm-up period; immediately before beginning a new activity in the workout routine; etc.). In some instances or under some conditions, the user interface system may ask for user input indicating whether a workout activity (or an overall workout routine) should be extended (e.g., by a certain time period, by adding one or more songs to an existing workout routine or activity, etc.).

When appropriate (e.g., in response to the user's input), the processing system may provide a revised workout routine or modify at least one parameter of the existing workout routine in a wide variety of different ways. For example, based on the user's input, the workout routine may be revised or modified by: increasing a time period associated with at least one workout activity in the workout routine; decreasing a time period associated with at least one workout activity in the workout routine; increasing a resistance level associated with use of a piece of exercise equipment for at least one workout activity in the workout routine; decreasing a resistance level associated with use of a piece of exercise equipment for at least one workout activity in the workout routine; increasing workout speed associated with use of at least one piece of exercise equipment used in the workout routine; decreasing workout speed associated with use of at least one piece of exercise equipment used in the workout routine; increasing a hill climb, step count goal, or elevation change parameter associated with use of at least one piece of exercise equipment used in the workout routine; decreasing a hill climb, step count goal, or elevation change parameter associated with use of at least one piece of exercise equipment used in the workout routine; increasing a distance parameter or goal associated with at least one workout activity in the workout routine; decreasing a distance parameter or goal associated with at least one workout activity in the workout routine; adding one or more workout activities to the workout routine; removing one or more activities from the workout routine; and/or changing activities or goals in the workout routine. Other ways of modifying or revising a workout routine are possible without departing from the invention.

Additional aspects of the invention relate to methods for tracking and/or controlling workout routines or activities included in athletic performances (e.g., methods performed by the various systems described above, such as methods performed in or by one or more of the user's portable equipment (e.g., carried during the workout routine) and/or one or more personal computers and/or remote computers to which the user's portable equipment may be connected and send data and/or from which the user's portable equipment may receive data). Examples of such methods and steps included therein are described above in terms of operating the example systems described above, and they also are described in more detail below.

Still additional aspects of this invention relate to user interfaces used to operate the athletic performance tracking and/or control systems, receive user input, and/or perform athletic performance tracking and/or control methods, e.g., including the systems and methods described above. User interfaces in accordance with at least some examples of this invention may be provided on one or more of the user's portable equipment (e.g., carried during the workout routine) and/or one or more personal computers and/or remote computers to which the user's portable equipment may be connected and send data and/or from which the user's portable equipment may receive data. Such user interfaces and example components and features thereof generally are described above in terms of operating the systems and performing the methods described above, and they also are described in more detail below.

B. Athletic Performance Tracking Systems, Methods, and User Interfaces that Utilize Subjective User Input Another aspect of this invention relates to athletic performance tracking systems, methods, and computer presented user interfaces. Such systems may include: (a) a processing system programmed and adapted to receive input indicating at least a first parameter associated with a user's athletic performance during a workout routine (e.g., physical or physiological data associated with the workout routine, such as speed information, distance information, timing information, heart rate information, pulse rate information, etc.); and (b) an input system that receives user input ranking or characterizing an intensity or difficulty of the workout routine. The processing system further may be programmed and adapted to present objective data to the user relating to the workout routine (e.g., speed information, distance information, timing information, heart rate information, pulse rate information, etc.). Using the user's subjective input (and optionally the objective data, when present), systems and methods according to at least some examples of this invention may better design future workout routines or parameters, e.g., to help better maintain user interest, to help users better improve their fitness and/or reach their fitness goals, and/or to help prevent soreness, overtraining, etc.

Systems according to at least some examples of this invention further may include a storage system that stores data relating to plural workout routines performed by the user and/or stores the user input ranking or characterizing the intensity or difficulty of the respective workout routine.

Such storage systems may constitute part of the user's portable equipment (e.g., equipment carried by the user and/or used during the course of a workout routine), or they may be provided as part of a remote system, such as a user's personal computer and/or a remote networked computer (optionally a computer to which at least some portion of the user's portable equipment may be connected or from which at least some portion of the user's portable equipment will ultimately send and/or receive data).

Athletic performance tracking systems according to at least some examples of this invention further may include a workout routine design system for designing future workout routines based, at least in part, on the user input ranking or characterizing the intensity or difficulty of a workout routine. For example, for workouts ranked as "too hard" or "too intense," systems according to at least some examples of the invention may design future workouts to be somewhat less difficult or intense (e.g., to help prevent soreness, overtraining, discouragement, etc.). On the other hand, for workouts ranked as "too easy," systems according to at least some examples of this invention may design future workouts to be somewhat more difficult, e.g., to help the user better or more quickly improve their fitness and/or achieve their fitness goals.

Additional aspects of the invention relate to methods for tracking athletic performances (e.g., methods performed by the various systems described above, such as methods performed in or by one or more of the user's portable equipment (e.g., carried during the workout routine) and/or one or more personal computers and/or remote computers to which the user's portable equipment may be connected and send data and/or from which the user's portable equipment may receive data). Examples of such methods and steps included therein are described above in terms of operating the example systems described above, and they also are described in more detail below.

Still additional aspects of this invention relate to user interfaces used to operate the athletic performance tracking systems, receive user input, and/or perform the athletic performance tracking methods, e.g., including the systems and methods described above. User interfaces in accordance with at least some examples of this invention may be provided on one or more of the user's portable equipment (e.g., carried during the workout routine) and/or one or more personal computers and/or remote computers to which the user's portable equipment may be connected and send data and/or from which the user's portable equipment may receive data. Such user interfaces and example components and features thereof generally are described above in terms of operating the systems and performing the methods described above, and they also are described in more detail below.

C. Athletic Performance Sensing Systems with Media Content Control Including Use of Subjective User Input Another aspect of this invention relates to athletic performance sensing systems that include media content presentation, e.g., as part of a workout routine (optionally, with media content data or data identifying desired media content included as an integral part of data providing or setting forth a desired workout routine). Users may create their own workout routines or download existing routines, and they may further control (or "mix") the media content to be played or presented during the course of the workout routine. The data providing or setting forth the workout routine information additionally may include the data for presenting the desired media content or data pointing to memory location (optionally from an external source) and/or allowing retrieval or presentation of the desired media content. In addition, however, systems, methods, and computer interfaces according to at least some examples of this invention may allow users to input their subjective reaction to media content presented during the workout routine. Such systems may include, for example: (a) a processing system programmed and adapted to receive input indicating at least a first parameter associated with a user's performance during a workout routine, wherein the first parameter includes physical or physiological data associated with the workout routine (e.g., speed, distance, timing, pulse rate, and/or heart rate information, etc.); (b) a media content presentation system for retrieving and/or presenting media content to a user during the workout routine (e.g., a video display, an audio display (such as an MP3 or other music playback device, etc.), etc.); and (c) an input system that receives user input ranking or characterizing a user's subjective reaction to the presented media content. The user input may be used, at least in part, to control future disposition of the media content (e.g., increasing its playback frequency, decreasing its playback frequency, eliminating it from the play library, elevating it to a "motivational song" or an "ultimate motivational song," etc.).

The processing system in at least some examples of this aspect of the invention further may be programmed and adapted to: (a) correlate features of the presented media content with at least one physical or physiological parameter associated with the user's performance during the workout routine, and/or (b) display objective data including information relating to this parameter. In this manner, if desired, before changing the status of and/or future disposition of media content, users also can look at the objective data relating to their workout to see how, if at all, the media content affected their performance (e.g., did performance improve during play of that media content, etc.).

Additional aspects of the invention relate to methods for sensing athletic performance data (e.g., methods performed by the various systems described above, such as methods performed in or by one or more of the user's portable equipment (e.g., carried during the workout routine) and/or one or more personal computers and/or remote computers to which the user's portable equipment may be connected and send data and/or from which the user's portable equipment may receive data). Examples of such methods and steps included therein are described above in terms of operating the example systems described above, and they also are described in more detail below.

Still additional aspects of this invention relate to user interfaces used to operate the athletic performance sensing systems, receive user input, and/or perform the athletic performance sensing methods, e.g., including the systems and methods described above. User interfaces in accordance with at least some examples of this invention may be provided on one or more of the user's portable equipment (e.g., carried during the workout routine) and/or one or more personal computers and/or remote computers to which the user's portable equipment may be connected and send data and/or from which the user's portable equipment may receive data. Such user interfaces and example components and features thereof generally are described above in terms of operating the systems and performing the methods described above, and they also are described in more detail below.

II. Specific Examples of the Invention

While example aspects and features of this invention generally have been described above, the following detailed description, in conjunction with FIGS. 1-19, provides even more detailed examples of electronic devices and athletic performance sensing systems and methods in accordance with examples of this invention, as well as example user interfaces for operating such systems and performing such methods. Those skilled in the art should understand, of course, that the following constitutes descriptions of examples of the invention and should not be construed as limiting the invention.

A. Description of Various Components of Example Sensing Systems According to this Invention FIG. 1 illustrates example systems and an environment in which various aspects of the present invention may be used. As shown in FIG. 1, a person 100 involved in an athletic performance or workout activity may have one or more sensing devices 102(a), 102(b), 102(c), and 102(d) included on their person, their clothing, their footwear, their equipment, etc. These sensing devices may sense data associated with the athletic performance, including, for example, physical or physiological data associated with the athletic performance. As some more specific examples, in the environment illustrated in FIG. 1, sensors 102(a) and/or 102(b) may sense step count and data associated with such activities (e.g., for pedometer type speed and/or distance measuring), GPS data (e.g., location and/or altitude data, time data, etc.), step impact force data (e.g., for active impact attenuation control), jump height data, or the like. Sensor 102(c) may sense pulse rate, body temperature, blood pressure, hydration levels, or the like, and sensor 102(d) may sense heart rate, EKG data, and the like. Of course, any number of sensors may be provided, and such sensors may sense any desired type of athletic performance information (e.g., one or more physical or physiological parameters) without departing from this invention. Additional examples of potential types of data relating to an athletic performance that may be sensed and/or collected include, but are not limited to: route data; ambient temperature data; ambient humidity data; barometric pressure data; sole member compression data; air intake rate or volume data; air expel rate or volume data; EEG data; blood gas content data; and the like.

As will be described in more detail below, users 100 of systems and methods according to examples of this invention may be involved in a wide variety of different athletic performance and/or workout activities, including, for example: various activities using training machines (e.g., in a gym), such as treadmills, spinning machines, elliptical training machines, stationary bicycles, stair climbing machines, cross-country ski simulating machines, weight lifting machines, rowing machines, etc.; and various athletic activities that may or may not directly involve the use of training machines or other equipment, such as running, walking, yoga, dance, pilates, stretching, weight lifting (with free weights), martial arts training, tae bo, boxing, wrestling, crew, rowing, kayaking, team based sports (such as baseball, softball, basketball, football, soccer, etc.), athletic track and field events, etc. Systems and methods according to at least some aspects of this invention may receive input data indicating the type of activity in which the user is involved, e.g., through a manual user input, automatically via electronic communication with some portion of the systems according to the invention, semi-automatically in response to a user's command, etc., as will be described in more detail below.

The various sensors, e.g., 102(a) through 102(d), also may be portable and carried by the person 100 in any desired manner without departing from this invention. For example, if desired, one or more sensors may be mounted in or on an article of footwear 104 (e.g., like sensors 102(a) and 102(b) in this illustrated example), provided in or on an article of athletic apparel (e.g., like arm band 106 in this example, which includes sensor 102(c), in a shirt, shorts, pants, socks, headband, etc.), and/or carried along on a piece of athletic equipment (e.g., like a bicycle, bat, racket, club, vehicle, ball, etc.). As still additional examples, as illustrated in FIG. 1, a sensing device 102(d) may be mounted directly on the athlete's 100 body, e.g., by adhesives, bands, hooks, other mechanical connectors, or the like.

The sensing systems and/or devices 102(a) through 102(d), as well as any data transfer systems associated therewith (e.g., such as wireless transmission or transceiver devices 108 shown in FIG. 1 and described more below (e.g., RFID elements, radio transceivers, etc.)), may be mounted on and/or in articles of footwear, clothing, athletic equipment, adhesive substrates, or the like in any desired manner, e.g., via clips, clamps, adhesives, sewing, in pockets, in suitable receptacles, via hook-and-loop fasteners, via other fasteners or mechanical structures, etc. Alternatively, if desired, the sensing systems or devices 102(a) through 102(d) may be integrally formed with and/or included as part of an article of footwear, an article of clothing, a piece of athletic equipment, etc. without departing from the invention (e.g., mounted therein, optionally in a permanent or freely removable manner, etc.) If desired, one or more sensing devices and its/their associated data transfer system (s) 108 may be included as part of a single structure, e.g., mounted in a common housing and/or on a common printed circuit board, connected to one another, etc., without departing from this invention. Further, if desired, the housing (if any) may be equipped with an ON/OFF switch; with operation lights (e.g., LEDs, etc.) or other indicators, e.g., to indicate power status (e.g., on/off), power source status (e.g., charging v. battery operation), remaining battery life, data reception and/or processing status (e.g., standby v. receiving v. transmitting v. processing, etc.), charge or recharging level status, etc.; etc.

In accordance with at least some examples of this invention, physical or physiological data associated with an athletic performance may be collected by the various sensing devices (e.g., devices 102(a) through 102(d)) and transmitted to an output device 110 for display or other output (and optionally storage, further processing, etc.). Any type of output device 110 may be used without departing from the invention, including, for example, conventional or "off the shelf" output devices 110. More specific examples of suitable output devices 110 include: electronic devices with a display screen, such as an LED, LCD, or plasma display screen; watches; portable audio or other media content storage and/or playback devices with an audio output, visual display, or other output, such as radios, tape players, CD players, MP3 players, handheld computing devices, and the like; alphanumeric display devices, such as beepers, pagers, and the like; portable video or audio/video display devices, such as portable televisions, DVD players, and the like; portable communication devices, such as cellular telephones, radios, and the like; portable computing systems, such as PDAs, hand top or palm top computing systems, and the like. In the illustrated example, the output device 110 includes an audio or other media content playback device (such as an IPOD® (commercially available from Apple Computer, Inc., of Cupertino, Calif.)) that the user 100 has engaged with his belt or clothing so as to be readily carried and used during the athletic performance. The use of this type of arrangement is advantageous in at least some situations because the athletic performance data may be displayed on the display system of the device 110 and/or transmitted to the user 100 via the headphones 140 or other audio output device, and thus the user need not obtain and/or carry an independent display device to enable display or transmission of the athletic performance data (thereby reducing weight, expense, and handling difficulties).

One cannot just simply begin transmitting athletic performance data from sensing devices 102(a) through 102(d) to a conventional electronic device 110 and expect the device 110 to operate to receive this data and display it in the desired format (and/or in a user controllable form or format). Accordingly, as illustrated in FIG. 1 and in more detail in FIG. 2, systems and methods in accordance with at least some examples of this invention may include an electronic interface device 112 that physically plugs into the electronic device 110 (e.g., in a releasable manner) and is carried along with the electronic device 110 during the athletic performance. As shown in more detail in FIG. 2, the electronic interface device 112 of this example includes a connector system 114 that physically plugs into and connects with conventional input ports 116 provided on this electronic device 110 model. The input port 116 into which the connector system 114 of the interface device 112 connects may be any type of input port provided on an electronic device 110, such as data input ports (e.g., parallel ports, serial ports, USB ports, earphone or other jacks or ports, etc.), e.g., like input ports used in conventional electronic devices for data input, synchronization, recharging, AC power supply, etc. The connector system 114 may include suitable connecting devices, such as wires, pins, electrical connectors, and the like, so as to make electrical connection or other suitable connections with corresponding elements provided in the input port 116 of the electronic device 110 (e.g., to allow electronic and/or data communications between the interface device 112 and electronic device 110). If necessary or desired, additional securing elements may be provided to securely hold the interface device 112 together with the electronic device 110, such as straps, hooks, buckles, clips, clamps, clasps, retaining elements, mechanical connectors, and the like.

Figure 2:
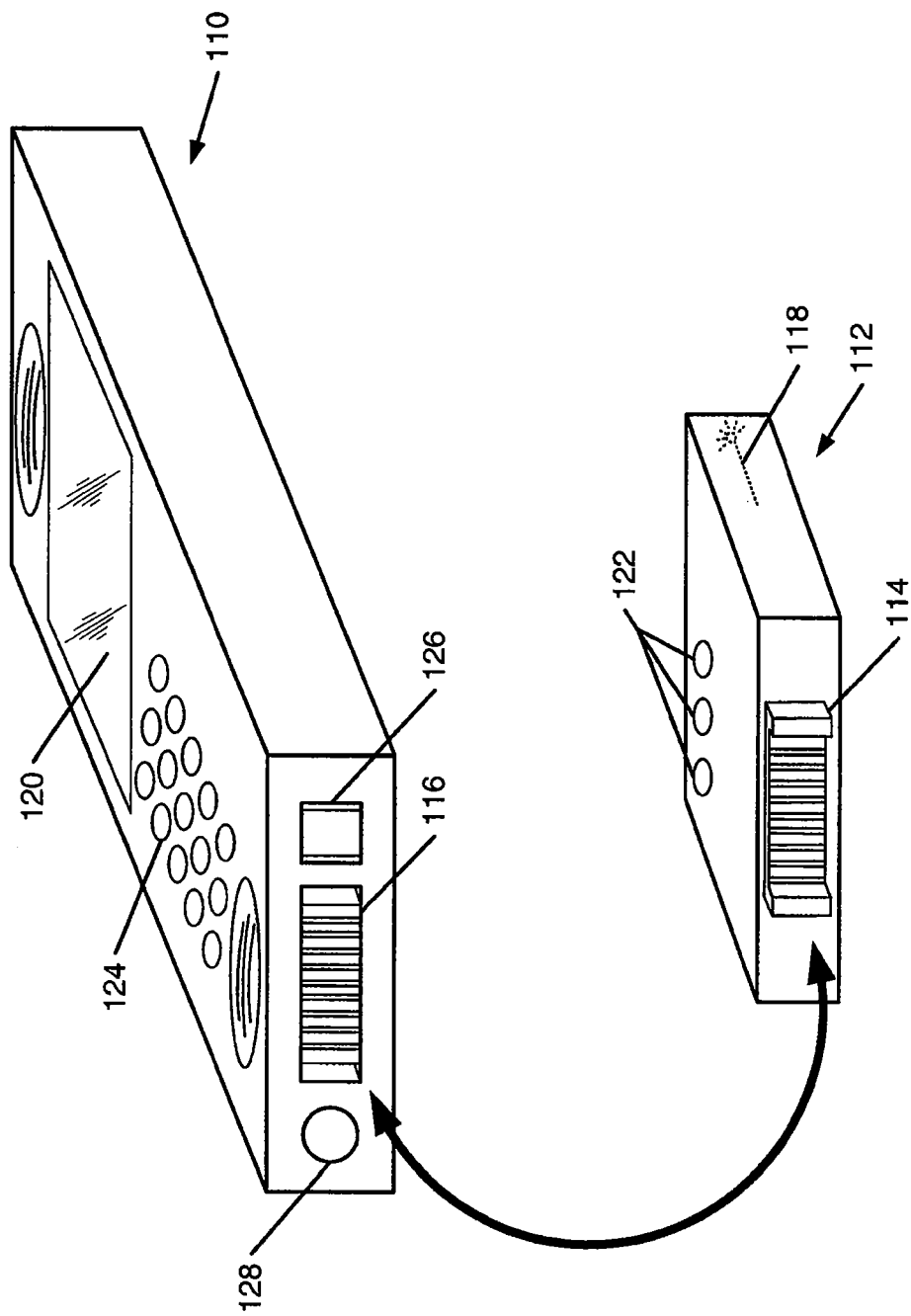
FIG. 2 illustrates an example electronic interface/output or display device combination in accordance with at least some examples of this invention.

In operation, the electronic interface device 112 may receive signals from one or more external sources, such as the various sensing devices 102(a) through 102(d), e.g., transmitted via data transfer systems 108 included with the sensing devices 102(a) through 102(d) to a data receiving device or system 118 provided in or with the interface device 112 (e.g., a wireless receiver or transceiver device, a radio transceiver, infrared receiver, light source receiver, etc.). If desired, data transfer system 108 and data receiving system 118 each may include the capability of receiving input data and transmitting output data without departing from this invention (of course, separate reception and transmission devices or systems may be provided on each of the sensing devices 102(a) through 102(d) and interface device 112, if necessary and/or desired). While a wireless communication protocol is illustrated in FIGS. 1 and 2, any desired manner of communicating between the sensing devices 102(a) through 102(d) and the interface device 112 may be used without departing from the invention, including wired connections, if desired. Signals from the sensors 102(a) through 102(d), optionally after data processing in the interface device 112 to place them in a form or format for display and/or use by the display device 110, are transferred from the interface device 112 to the electronic device 110 via connector system 114 (which is physically plugged into input port 116 of the electronic device 110 in this illustrated example). Once input to the electronic device 110, the input data may be further processed if necessary or desired and then displayed to the user in desired form on the display panel 120.

Any desired way of placing data derived from the physical or physiological data from the sensing devices 102(a) through 102(d) in the proper form or format for display on or output from electronic device 110 may be provided without departing from the invention. As examples, if desired, the interface device 112 may be specially designed and/or programmed for use with one or more specific electronic devices 110 (e.g., pre-programmed and/or wired to operate with a specific device or devices (e.g., specific models, etc.) and to provide output data in a form and format suitable for those devices). In this situation, the interface devices 112 may be marketed and sold specifically targeted to certain electronic devices 110. As another alternative, if desired, the interface devices 112 may be programmed at a later time to operate with a wide variety of different electronic devices 110, e.g., by downloading display or device driver and/or format data for specific electronic devices 110 from the internet, from disk, or from another source, etc. As a more specific example, when the user plugs the interface device 112 into an electronic device 110 (e.g., for the first time), signals exchanged between the interface device 112 and the electronic device 110 may identify the devices to one another and/or otherwise enable the processing system of one of the devices to activate or download driver or set up information, e.g., from a remote or external source, such as the internet, from a disk, from memory included with the interface device 112, etc., e.g., akin to the manner in which personal computer devices recognize newly attached hardware (e.g., a mouse, printer, scanner, etc.) and/or perform various setup operations associated with newly added hardware or software. Of course, other ways of assuring that the data is placed in proper form or format for display, audio output, or other output may be used without departing from this invention. The processing to place the data in the form and/or format for display or other output may take place in the interface device 112, in the electronic device 110, in the sensor devices 102(a) through 102(d), and/or in any other desired component or system without departing from this invention.

If desired, in accordance with at least some examples of this invention, the electronic interface device 112 further may include a user input system 122, such as one or more rotary input devices, switches, buttons (as shown in the illustrated example in FIG. 2), mouse or trackball elements, touch screens, or the like. This user input system 122 may be used, for example: to control one or more aspects of the processing of the input data received via data receiving device 118, to control input data receipt (e.g., timing, types of information received, on-demand data requests, etc.), to control data output to or by the electronic device 110, to control the sensing devices 102(a) through 102(d) (e.g., activating or deactivating them, etc.), etc. Alternatively or additionally, if desired, the input system on the electronic device 110 (e.g., buttons 124, a touch screen, a digitizer/stylus based input, a rotary input device, a trackball or roller ball, a mouse, etc.), may be used to provide user input data to the interface device 112 and/or to the sensing devices 102(a) through 102(d) or the sensing systems (e.g., if the connector system 114 or other portion of the interface device 112 is designed to accept input from the electronic device 110). As still another example, if desired, a voice input system may be provided with the interface device 112 and/or the electronic device 110, e.g., to enable user input via voice commands. Any other desired type of user input system, for control of any system elements and/or for any purpose, may be provided without departing from the invention.

The electronic device 110 may include additional input and/or output elements, e.g., such as ports 126 and 128 shown in FIG. 2, e.g., for headphones (or other audio output), power supplies, wireless communications, infrared input, microphone input, or other devices. If desired, and if these ports 126 and/or 128 would be covered when the interface device 112 is attached to the electronic device 110, the interface device 112 may be equipped with similar external ports to ports 126 and/or 128, and internal circuitry may be provided in the interface device 112 to enable the user to plug the same additional devices into the interface device 112 as they might plug into the electronic device 110 and still take advantage of the same functions (e.g., to thereby allow the necessary data, signals, power, and/or information to pass through the interface device 112 to the user, to another output, and/or to the electronic device 110).

Figure 3:
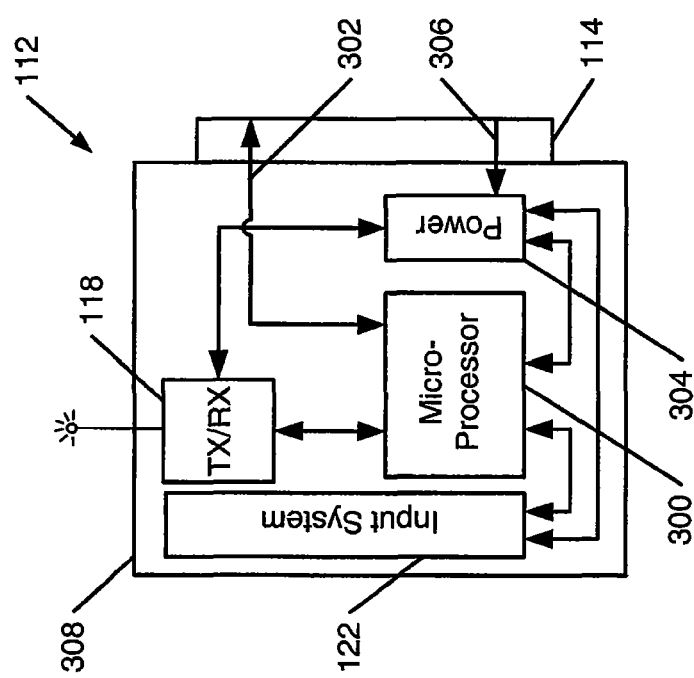
FIG. 3 illustrates a schematic diagram showing components provided in one example of an electronic interface device in accordance with this invention.

FIG. 3 includes a schematic diagram of various example components that may be included in an electronic interface device 112 in accordance with at least some examples of this invention. As shown in FIG. 3 and described above in conjunction with FIGS. 1 and 2, the interface device 112 may include a connection system 114 for physically connecting to an electronic device, and a data transmission and/or reception system 118 (e.g., a wireless data receiver or transceiver, an infrared receiver, RFID receiver, etc.) for receiving input data from an external source, such as a sensor for sensing athletic performance data, a computer, network, or other processing system, etc. Additionally, as further shown in FIG. 3, the interface device 112 may include an input system 122 for receiving user input, e.g., via keys, buttons, touch screen, digitizer, voice input, stylus input, rotary dial input, trackball or roller ball input, mouse input, switches, etc.

In accordance with at least some examples of this invention, the electronic interface device 112 further may include a processing system, e.g., microprocessor 300, for performing various operations, e.g., for operating the electronic interface 112, for interacting with the external data source(s), for receiving user input from one or more sources (e.g., via input system 122, via computer or network connections, via transceiver 118, etc.), for interacting with the electronic device 110 (e.g., via output supplied to the electronic device 110 through wire or pin connections 302 included with the connection system 114), etc. Any number of wire, pin, or other connections may be provided via connection system 114 to provide suitable electronic/data communications between the interface device 112 and an external electronic device 110 (e.g., like the connection systems provided on cellular telephones, MP3 players, audio/video playback devices, PDAs, or other portable electronic devices, including conventional electronic devices known and commercially available). The connector system 114 may be designed to match the electronic device 110 into which it plugs so as to provide a path for electronic/data communications between the interface device 112 and the electronic device 110. Moreover, if desired, microprocessor 300 may include operating system software and/or may process the input data from the sensing device(s) 102(*a*) through 102(*d*), in accordance with at least some examples of this invention, to transform the data into suitable forms for receipt by, use in, display by, and/or output by the electronic device, to change the data form or format, to make calculations based on the raw input data, etc.

FIG. 3 further illustrates a power supply device 304 included as part of the electronic interface device 112. This power supply device 304 may include a conventional battery, e.g., a rechargeable or long life battery, as are commonly known and used in the electronics art. Alternatively or additionally, if desired, the power supply device 304 may receive power input from the electronic device 110 to which it is attached (e.g., through input pin, wire, or line 306 or other connection system) and use the power source from the electronic device 110 to operate the various elements and components in the interface device 112 (e.g., the microprocessor 300, the data receiving system 118, the input system 122, any operating lights or displays, and the like). As still another example, if desired, the power supply 304 may connect to an external power source, such as an AC power supply, an external battery power source, etc., optionally for recharging a rechargeable battery.

If desired, some or all of the various parts illustrated in FIG. 3 may be mounted, housed, or contained in or on a housing system 308, formed in or on a common printed circuit board, or otherwise formed as a convenient module or package. The connection system 114 may at least partially extend out of the housing 308, may be integrally formed as part of the housing 308, may be a separate element fixed to the housing 308 (e.g., by adhesives or connectors, etc.), may be at least partially recessed within the housing, or otherwise may be available and/or included with the housing system 308.

Figure 4:
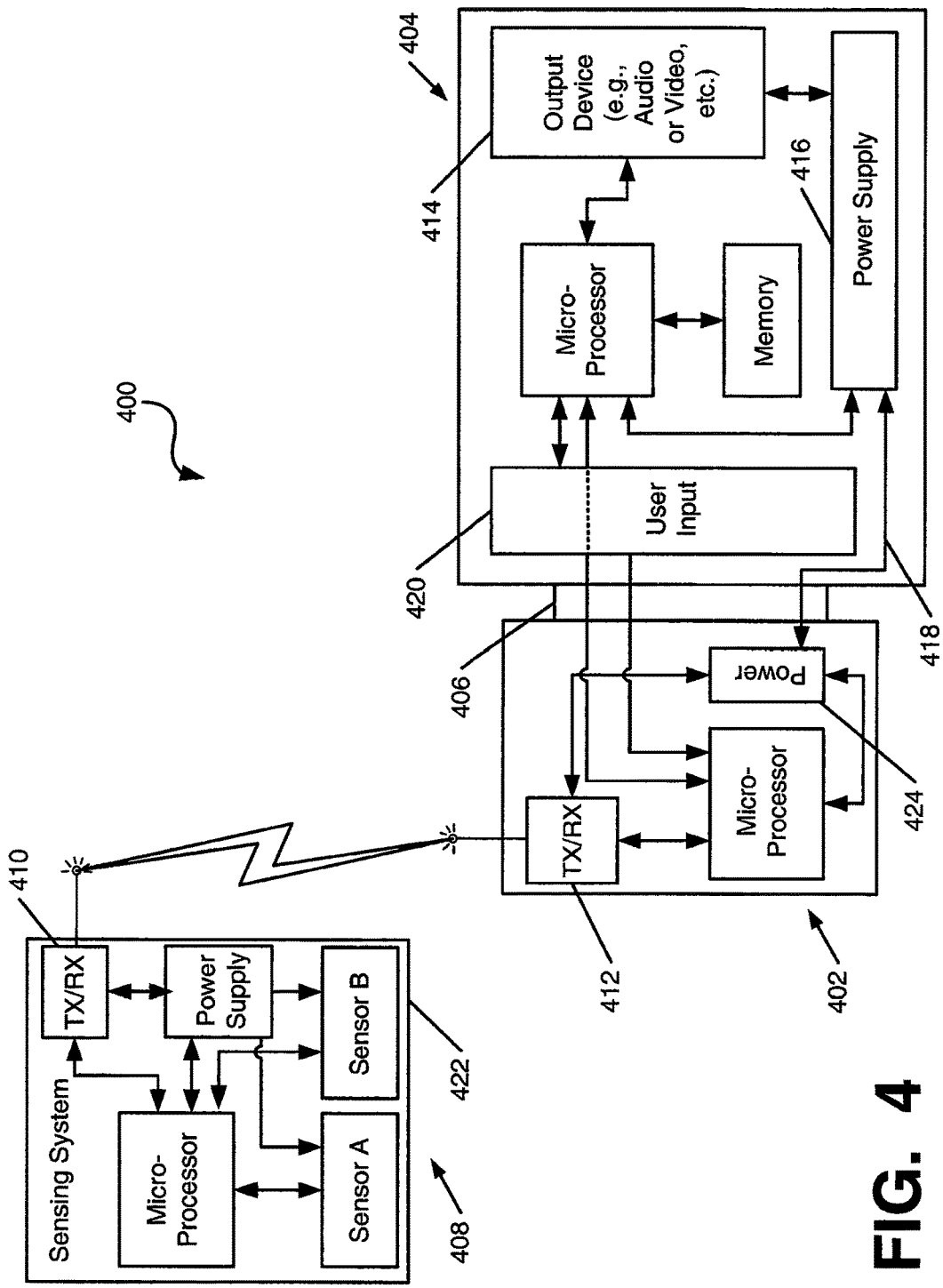
FIG. 4 illustrates a schematic diagram showing components provided in one example of an athletic performance sensing system in accordance with this invention.

FIG. 4 illustrates a schematic diagram of an overall athletic performance sensing or tracking system 400 in accordance with at least some examples of this invention. In this system 400, an electronic interface device 402 is physically plugged into a portable electronic device 404 via a mechanical connection system 406 that holds the two devices together, e.g., in a secure but releasable manner (e.g., via a friction fit, via detents or retaining elements, via spring elements, etc.). Optionally, if desired, other independent securing elements may be provided to at least partially help hold the interface device 402 with the portable electronic display device 404 (e.g., hooks, straps, snaps, clips, clamps, clasps, retaining elements, etc.).

This example system 400 further includes a sensing system 408 for sensing and transmitting some type of athletic performance data. More specifically, in this example structure, athletic performance data (e.g., physical or physiological data associated with an athletic performance) is sensed by sensors A and/or B, and data from these sensors is sent to the sensing system's processing system, e.g., a microprocessor, which optionally may cause the data to be stored (e.g., in a storage system or memory (not shown in FIG. 4)), further processed, etc. A power supply may be provided (within the system 408 module or external thereto) to operate the various components of the sensing system 408, such as the sensors, the microprocessor, the data transfer system 410, memory, and/or any other necessary or desired components. If desired, the microprocessor on board the sensing system 408, if any, may process the sensor data, change its form or format, or otherwise manipulate the data prior to sending it on to other parts of the system 400. The sensing system 408 may constitute a sensor module like modules 102(*a*) through 102(*d*) illustrated in FIG. 1.

At an appropriate or desired time (e.g., when a data request is received, periodically, automatically, upon user demand, etc.), the sensing system 408 may send at least some portion of its data (e.g., raw data directly from one or more of the sensors, data derived at least in part from the raw data, etc.) to the electronic interface device 402, e.g., for eventual output to a user via electronic device 404. This may be accomplished, for example, as shown in FIG. 4, via a wireless data transmission system (e.g., from wireless data transfer or transmission element 410 in the sensing system 408 to wireless data receiving element 412 in the electronic interface device 402) or in any other desired manner without departing from this invention. Any desired wireless protocol, broadcast protocol, or other data transmission protocol may be used without departing from this invention.

Once received at the electronic interface device 402, the athletic performance data may be further processed, if necessary or desired, and then supplied to the processing system (e.g., microprocessor) of the electronic device 404. This may be accomplished at any desired time or timing (e.g., when a data request is received, automatically, periodically, on user demand, etc.) without departing from this invention. From there, the data may be further processed, if necessary or desired, and then sent to an output device in a form suitable for output to a user (e.g., in audio, video, and/or alphanumeric form, etc.).

In this illustrated example system 400, power for the electronic interface device 402 is supplied via the power supply 416 used for operating the electronic device 404 (e.g., which may be a rechargeable battery of a cellular telephone, an audio playback device, or other portable electronic device), as shown by the connection 418 between the power supply 416 and the "power" element 424 via the connection system 406. The "power" element 424 in interface device 402 in this example may be a component used simply to distribute power from an external power source (e.g., the power supply 416 of electronic device 404 in this example) to various components of the interface device 402. Alternatively, the power element 424 may be omitted, e.g., if internal wiring of the interface device 402 allows power transfer from power supply 416 to all required components of the interface device 402. As still another example, if desired, power element 424 may constitute a rechargeable battery that may be recharged independently and/or through power supplied through power supply 416.

Additionally, in this example system 400, user input may be furnished to control the electronic interface device 402 via input systems 420 provided in the portable electronic device 404. For example, if desired, a user could enter a specific mode of operation via inputs provided on the electronic device 404 in which various features, functions, or characteristics of the electronic interface device 402 may be controlled. Additionally or alternatively, if desired, the electronic interface device 402 may include its own input system (and/or its own power supply), e.g., as described above in conjunction with FIG. 3, without departing from this invention (however, utilizing these components and resources from the electronic device 404 helps reduce the overall size, weight, and cost of the interface device 402 and system 400).

Of course, many different arrangements of various elements or components, including some or all of the elements or components shown in FIG. 4, may be used without departing from this invention. Moreover, additional components or elements may be included in such systems, or one or more of the illustrated components or elements may be eliminated without departing from the invention. Additionally, if desired, a single electronic interface device 402 and electronic device 404 may be simultaneously operatively connected so as to receive data input from multiple independent sensing systems, e.g., of the type shown at reference number 408 (see, for example, the arrangement of FIG. 1). As another example, if desired, a single sensing system 408 may communicate, separately or simultaneously, with plural interface devices 402 and/or electronic devices 404. Many variations in the overall structures, components, and architectures of various systems are possible without departing from this invention.

One potential advantage of systems and methods according to at least some examples of this invention lies in the fact that the components and infrastructure of an existing portable electronic device (e.g., a cellular telephone, MP3 player, PDA, or the like) may be leveraged and used in combination with an electronic interface device that connects thereto and electronically communicates therewith in order to allow this existing electronic device to additionally display, output, and/or provide athletic performance data to a user without requiring the user to obtain and carry another electronic device. As noted above, leveraging the input system and/or power supply of the existing electronic device used for its display can further reduce the size, weight, cost, and complexity of the interface device, thereby providing additional advantages. Of course, if desired, the separate interface device (e.g., 112 or 402) may be eliminated and a separate dedicated electronic device 404 may be provided for accepting and displaying athletic performance data (and optionally performing other desired functions). As yet another example, if desired, electronic device 404 may be constructed to directly accept input from sensing systems 408, thereby rendering interface device 402 unnecessary.

Figure 5:
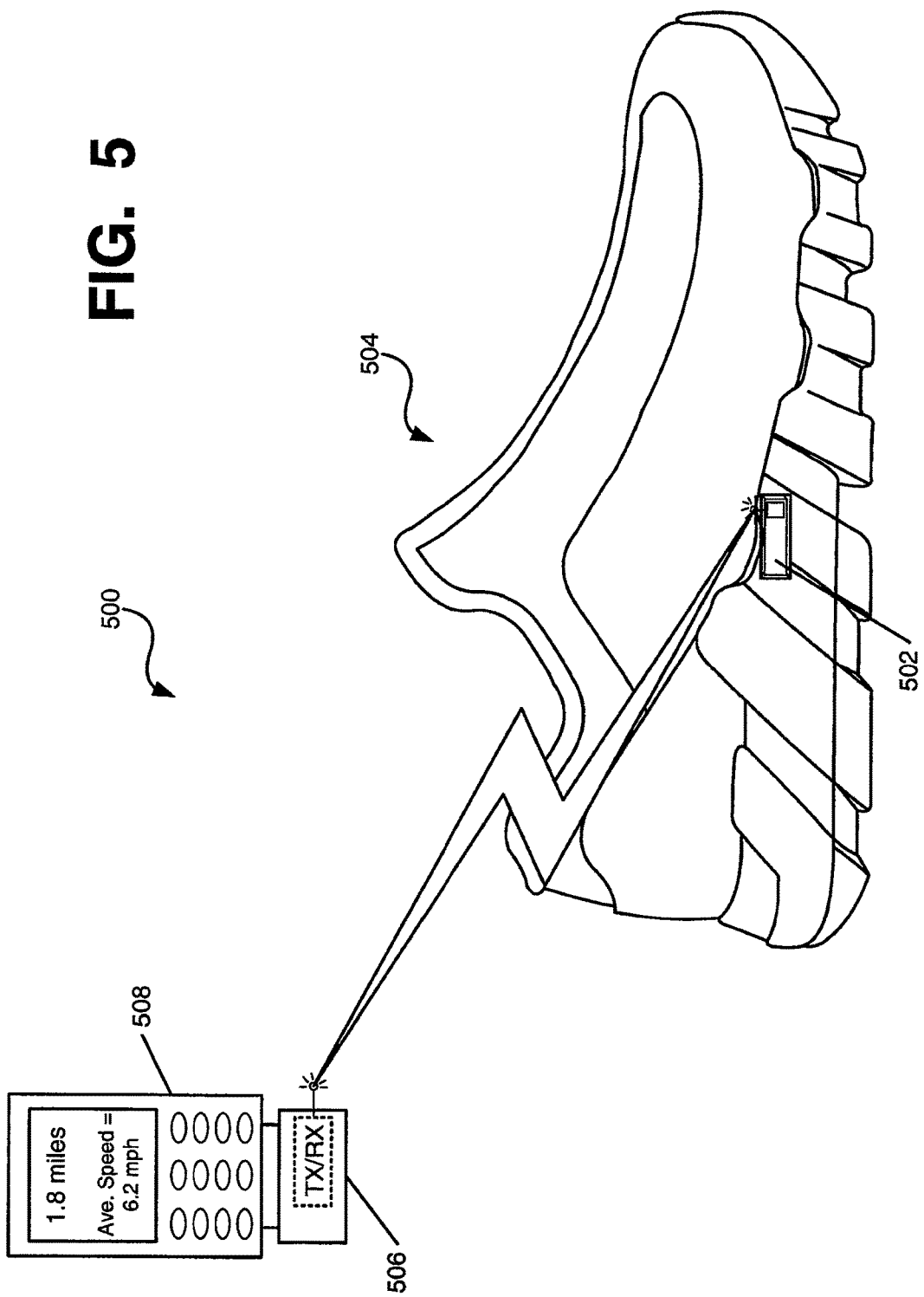
FIG. 5 illustrates an example of an athletic performance sensing system in accordance with this invention in which the athletic performance data sensor or collection device is mounted in an article of footwear.

Athletic performance sensing and/or tracking systems may be provided in a wide variety of different environments without departing from the invention. For example, as illustrated in FIG. 4, if desired, one or more sensors for sensing data associated with an athletic performance (e.g., physical or physiological data) may be provided in a housing 422, optionally along with at least a portion of a data transfer system (e.g., wireless transmission or transceiver device 410) and/or other processing or electronic components, e.g., to provide an athletic performance data sensing module or system 408. When provided as a module or otherwise provided as separate elements, these portions of athletic performance sensing systems (e.g., 408) may be provided at any desired location without departing from the invention, e.g., assuming their data sensing, processing, and/or transmitting capabilities are not compromised by the positioning. FIG. 5 illustrates an example system and environment 500 in which an athletic performance sensing module 502 is mounted in an article of athletic footwear 504. The module 502 may include, for example, one or more athletic performance data sensors, a data transfer system, processing capabilities, a power supply, and/or the like (e.g., like the system 408 shown in FIG. 4). Any desired manner of mounting the module 502 in or on the article of footwear 504 may be provided without departing from the invention, such as via a slot, chamber, or receptacle formed in the midsole (e.g., in the heel or arch portion); via a mounting pocket or element; via straps, adhesives, mechanical connectors, hook-and-loop fasteners, retaining elements, etc.; via user removable connections; etc. Alternatively, if desired, the module 502 may be embedded in or integrally formed as part of the article of footwear 504, e.g., during footwear manufacture, and/or permanently fixed thereto. As one more specific example, module 502 may be mounted in a receptacle formed in the heel or arch portion of an article of footwear (e.g., formed in a midsole member), beneath the footwear insole member, in a manner similar to the receptacles provided in "PLUS™ ready" footwear available from NIKE, Inc. of Beaverton, Oreg.

As further shown in FIG. 5, the module 502 may be in wireless (or other) communication with an interface device 506, which in turn is physically connected to an electronic device 508, such as a music playback device or a cellular telephone as illustrated in FIG. 5. This electronic device 508 may be attached to the user's body, clothing, or equipment, e.g., so as to be easily carried, moved, and/or viewed during the athletic performance. In general, any of the various athletic performance sensing systems, electronic interface devices, and/or portable electronic devices of the types described above in conjunction with FIGS. 1-4 may be used without departing from this invention. As more specific examples, if desired, the sensing devices aboard module 502 may provide step count, timing, and/or other data, and the electronic interface device 506 may process this data so as to provide pedometer type speed and/or distance data for output by electronic device 508. Of course, any type of data may be provided by modules 502 and any desired type of information may be displayed or otherwise output on electronic device 508 without departing from this invention.

Given this general description of a basic athletic performance data collection system in accordance with at least some examples of this invention, more detailed descriptions of example features, content, and use of systems and methods according to examples of this invention follow.

Figure 6:
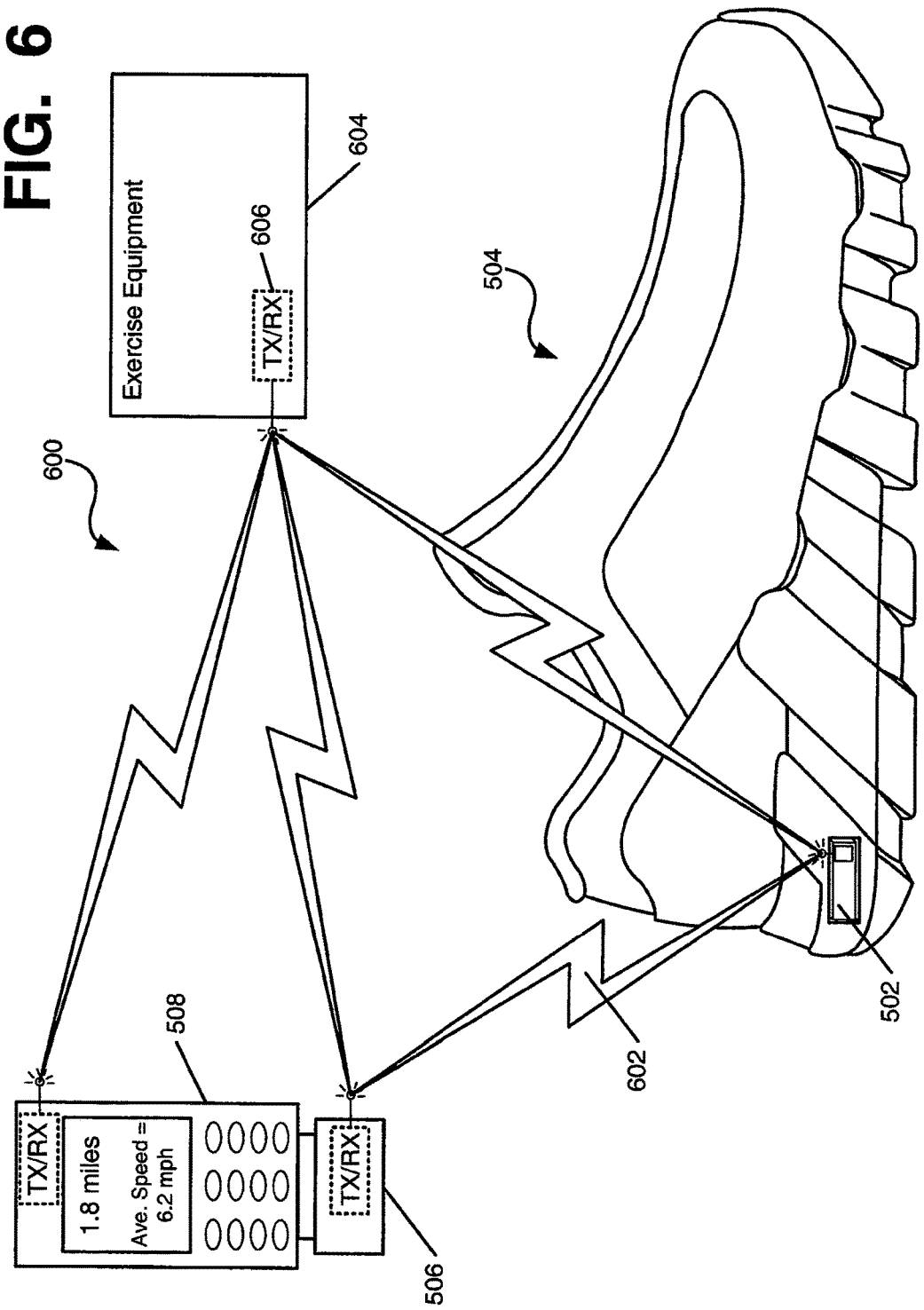
FIG. 6 illustrates an example of electronic communications between athletic performance sensing systems in accordance with at least some examples of this invention and external equipment.
Figure 7:
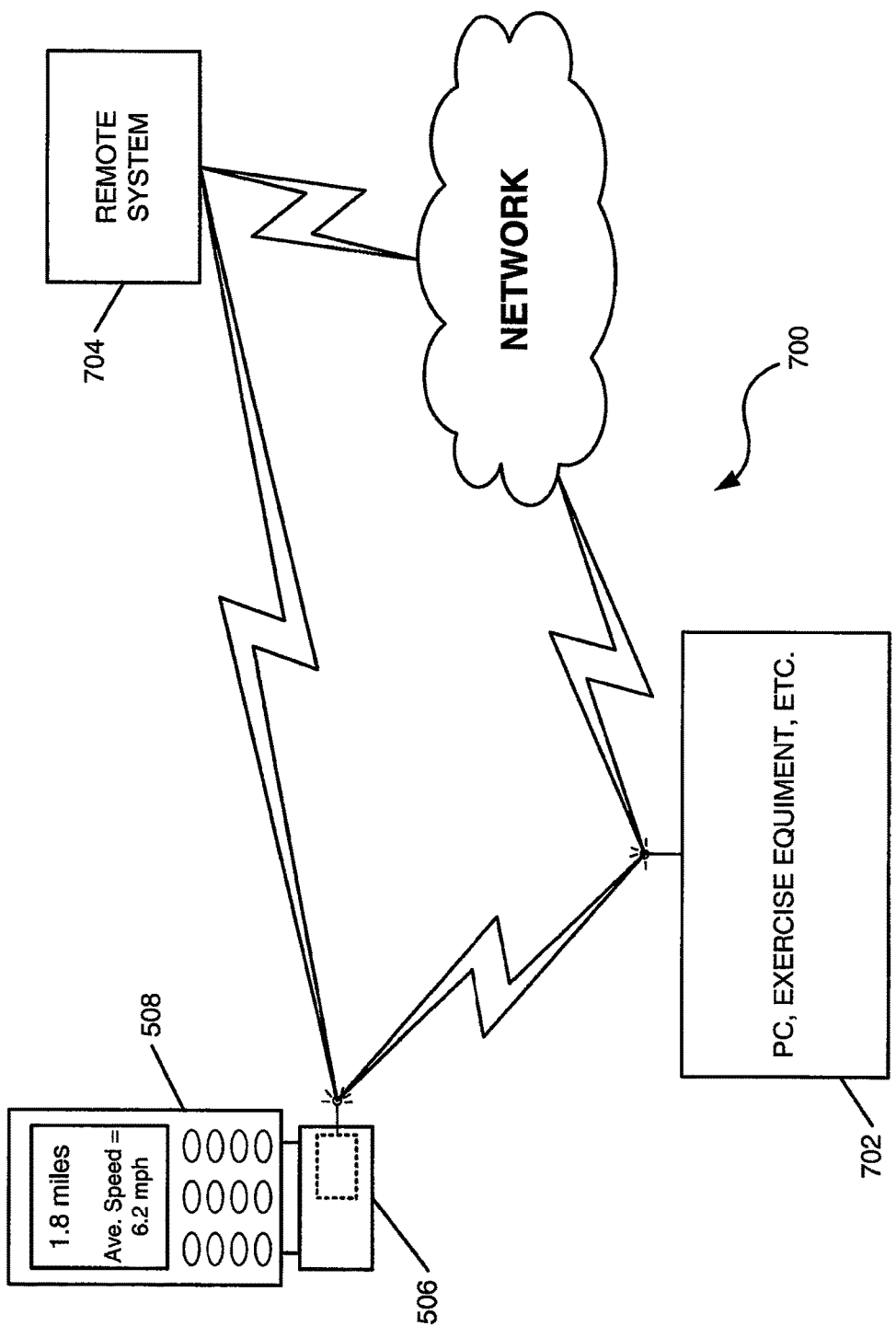
FIG. 7 illustrates an example of electronic communications between athletic performance sensing systems in accordance with at least some examples of this invention and remote systems, e.g., systems for storing, tracking, and/or analyzing the performance data and/or systems for providing workout routines and/or other data.

B. Description of Example Athletic Performance Sensing and Tracking Systems According to this Invention FIGS. 6 and 7 illustrate additional features of and environments of use for example performance sensing and tracking systems and methods in accordance with this invention. In addition to running or walking on an open course using pedometer based speed and distance information (or other sensed information), as illustrated in FIG. 1, systems and methods in accordance with at least some examples of this invention may be useful to sense and/or track athletic performance characteristics at other locales, such as in a gym or spa, in workout classes, at home, and the like. The system 600 of FIG. 6 illustrates the performance module 502 (e.g., carried by the athlete during the performance, such as in an article of footwear 504, as part of the athlete's clothing, an article worn by the athlete, etc.) in communication with a portable electronic device 508 via an interface device 506, e.g., as illustrated in FIG. 5. See transmission indicator 602 in FIG. 6. In addition to this communication, as illustrated in FIG. 6, any or all of the module 502, interface device 506, and/or electronic device 508 may be configured to exchange data with one or more pieces of exercise equipment 604 or other things, e.g., equipment or transceiver devices included in a gym, spa, or other athletic performance setting.

Reference number 604 in FIG. 6 may indicate any type of exercise equipment and/or gym, spa, home, or other athletic performance setting. For example, reference number 604 may represent a wide variety of different types of athletic and/or training equipment, including, for example: training machines commonly found in a gym, such as treadmills, spinning machines, elliptical training machines, stationary bicycles, stair climbing machines, cross-country ski simulating machines, weight lifting machines, rowing machines, etc. Additionally or alternatively, reference number 604 may represent various performance locales that may or may not directly involve the use of training machines, such as facilities (e.g., training rooms) used for yoga, dance, pilates, martial arts training, stretching, weight lifting, tae bo, boxing, wrestling, etc. As yet another example or alternative, reference number 604 may represent or include an input device through which a user can enter information regarding the athletic or training activities he/she has done or plans to do, such as track and/or field training or events, team sporting events, free weight lifting, etc. Reference number 604 also may relate to a physical or physiological parameter measuring system, such as a scale, heart rate monitor, blood pressure measuring system, body temperature measuring system, etc. Using systems like those illustrated in FIG. 6, users can use element 604 to produce input for tracking any desired type of athletic or training activity with which they are involved and/or physical or physiological parameter relating to their training.

A wide variety of different types of data and information may be exchanged between the exercise equipment 604 (or other workout or athletic performance setting or equipment) and the portable equipment kept by the user (e.g., module 502, interface device 506, and/or electronic device 508). For example, if desired, the equipment 604 may be designed to send information to the user's equipment (e.g., via transmission/reception system 606) relating to the workout parameters of an individual workout or training exercise, such as: data detectable or sensed by gym or workout equipment, such as distance traveled, speed, elevation changes, number of steps, number of floors climbed, overall time, speed or other data as a function of time, calories burned, revolutions per minute, number of rotations, resistance settings, hill or incline information, amount of weight lifted, number of repetitions, weight machines used, etc. Any measured physiological characteristics also may be sent to the user's portable equipment, such as heart rate, pulse rate, blood pressure, blood oxygen levels, EEG data, EKG data, body temperature, air intake/expel rates, etc. Transmission/reception system 606 also may send identification information, such as an exercise machine identification, room identification, location information, other equipment identification information, etc. The desired data may be sent to the user's portable equipment at any desired time, such as in real time (as it is being collected at the equipment 604), periodically, after the exercise is complete, as the user leaves the gym facility, etc.

For systems using pedometer based information, in addition to detecting speed and/or distance information, it is useful in at least some example systems and methods according to this invention for the sensing system to measure or detect data and information relating to the user's cadence, rhythm, or "beat" associated with the athletic performance activity (e.g., steps, rotations, foot movement direction changes, arm movement direction changes, etc., with respect to time, such as steps per second, revolutions per minute, stair-stepper steps per second, rowing strokes per minute, etc.). An accelerometer and/or direction change sensor may be used in determining cadence. The module 502 and/or other portions of the portable equipment (e.g., interface device 506 and/or electronic device 508) and/or the equipment 604 may be used to provide data and information relating to user cadence. Cadence information may be collected with respect to a wide variety of athletic performance activities, including many activities that take place in a gym using exercise equipment, such as running or walking on a treadmill, spinning, elliptical training, stationary bicycle training, stair-stepper training, cross-country skiing simulation, rowing simulation, etc. In addition to providing data relating to the athletic performance, cadence information also may be useful in systems and methods according to at least some examples of this invention for selection of motivational, inspirational, performance enhancing, or other media content during the athletic performance (e.g., for song selection and the like), as will be described in more detail below.

When reference number 604 represents a facility or locale, it may simply send information identifying the location and/or timing information (such as time spent at the location). For example, reference number 604 may include an RFID or other data transmission device 606 that communicates with the user's portable equipment to indicate when a user enters or leaves a certain room or area (such as a weight lifting room; an aerobics, yoga, or pilates studio; a martial arts training facility; etc.) and/or to indicate the amount of time the user spent at that location (such as actual entry and/or exit times, date information, overall time spent, etc.). If a specific locale may be used for numerous activities, scheduling or other information also may be provided and/or transmitted so that the transmission device 606 also may be capable of automatically transmitting the type of activity with which the user was involved when present at the location or facility. Such data can help users create and/or maintain a detailed tracking and/or complete log of their workout activities, e.g., even in situations where no physical or physiological data can be provided by the sensors. Optionally, if desired, users can include additional information in their workout calendar or log, e.g., for tracking purposes, such as user location data; flight or hotel stay information; menstrual cycle data; athletic event calendar information; target or goal date information; and any desired historical, future, calendar, or goal information.

Data also may be transferred from the user's portable equipment (e.g., module 502, interface device 506, and/or electronic device 508) to the exercise equipment or other workout or athletic performance setting 604. For example, user ID information may be transmitted so that the exercise equipment or other workout or athletic performance setting 604 can store workout data associated with the specific user. As another example, if desired, the user's portable equipment (e.g., module 502, interface device 506, and/or electronic device 508) may be used, at least in part, to control the exercise equipment or other workout or athletic performance setting 604, e.g., to make the workout machine settings correspond to a workout pre-programmed into or downloaded to the user's portable equipment. For example, workout information downloaded from a workout routine stored in or available through the portable equipment may be used to control various features of the workout, such as: weight machine settings, resistance settings, incline (or hill level) settings, target distance (or other overall time length or duration) settings, target calorie burn (or other physiological based parameter) settings, treadmill speed or incline settings, etc. As yet another example, if desired, the user's portable equipment may send workout identification information (e.g., Workout 12) to the exercise equipment or other workout or athletic performance setting 604, which then may use this identification information to provide the desired settings for the identified workout from information stored in memory. Data collected as a workout progresses (e.g., via module 502, etc.) also may be used, if desired, to control the exercise equipment or other workout or athletic performance devices (e.g., to set or change intensity or resistance levels, to shorten or lengthen workout times, etc.). Of course, other information also may be transmitted from the user's portable equipment to element 604.

As another potential option or alternative, if desired, the user's portable equipment (e.g., module 502, interface device 506, and/or electronic device 508) may be programmed and adapted to send information to the exercise equipment 604, e.g., for display by the exercise equipment 604, for transmission to a remote source (e.g., via a network maintained at the gym or spa, etc.), etc. As more specific examples, as described in more detail below, the electronic device 508 may be a playback device that presents audio and/or video information to the user, such as music, videos, and/or other entertainment content. If desired, systems and methods according to at least some examples of this invention may be arranged and adapted to send this content from or through the electronic device 508 (or other user carried portable equipment) to the exercise equipment 604 (or another device), so that the media (or other) content may be displayed or presented on a screen or other output device provided with the exercise equipment 604 (e.g., an input panel, a touch panel, a television screen, an audio output system, etc.). Furthermore, if desired, in such systems, the input panel or other portion of the exercise equipment 604 may be programmed and adapted to receive user input controlling the playback features of the media content (e.g., to skip songs or other content, replay songs or other content, select songs or other content for presentation, etc.).

FIG. 7 illustrates additional features that may be present in example athletic performance sensing and/or tracking systems and methods according to this invention. The arrangement 700 shown in FIG. 7 allows users to send data and information to and/or receive data and information from one or more remote sources, such as from one of the portable devices (e.g., module 502, interface device 506, and/or electronic device 508) to a personal computer (e.g., at the user's home or office) or other computer station 702 (which may include the workout equipment itself and/or a computer maintained at the gym or other facility) and/or to a remote system 704 (optionally via a network connection, such as over the Internet), which may be maintained and operated by the user, by a fitness center, by a gym, or by another third party. This arrangement 700 may allow for more convenient storage, maintenance, retrieval, and further processing of the collected athletic performance data (e.g., as compared to limiting the user interface, data processing, and/or computational capabilities of the overall system to operations performed through the electronic device 508 and/or interface 506).

In addition to storing historical data and information, this arrangement 700 allows downloading of data and information from one or more remote systems 704 to the user, e.g., to the PC or other equipment 702 and/or to the portable device 508 (optionally through the interface device 506). Data also may originate in the PC or other equipment 702 (without the use of a remote computer 704) and be sent to the user's portable equipment 506 and/or 508. In some instances, the remote system 704 (or system 702) may be accessed by multiple users (e.g., over a network, such as the internet or a gym based network), and such systems may provide a wide variety of data and information to users (e.g., each individual user may have his/her own webpage(s), user ID, password, etc.). While potential content of this exchanged data and information will be described in more detail below in conjunction with FIGS. 8 through 19, as examples, this downloaded data and information may include: pre-programmed workouts; music or other audio/video content; pre-programmed workouts mixed with music or other audio/video content including coaching and/or motivational content; comparative data; coaching, safety, and/or motivational content; and the like.

C. Description of Example Features of Systems and Methods According to this Invention One feature of systems and methods according to at least some examples of this invention relates to the ability to sense and track information relating to a wide variety of types of athletic performance activities. Data relating to athletic performances can be entered into systems and methods according to the invention automatically, semi-automatically, and/or manually. More specific examples follow.

When performing athletic activities using exercise machines (e.g., like those present in a gym, spa, home, etc.), users can get immediate feedback, data, and information relating to their activities on their portable electronic device 508, including data and information produced by the module 502 and/or data and information collected or measured by the exercise or other equipment 604. This may be accomplished, for example, using a system 600 like that shown in FIG. 6. If desired, the equipment 604 may transmit (automatically, in response to user input, in response to activation of an RFID transmission system, etc.) some type of identifying data or information so that the electronic device 508 or other portion of the user carried portable equipment can store information to track one or more of: the type of workout activity (e.g., type of machine, etc.), the length of the workout, one or more parameters associated with the workout, etc.

Some athletic performance activities do not utilize machines, but they may be performed in a specially designated room or area of a building or facility. As described above, a transmission device (e.g., device 606) may be provided at the locale to automatically, semi-automatically, or manually transmit data indicating the location or room at which the user was present, optionally along with the type of activity that took place while there (e.g., based on schedule or other information, for example, to indicate that the user participated in a dance class, pilates class, aerobics class, martial arts training, lifted weights, etc.). The room may include a wireless transmission system (optionally activated by an individual user, e.g., by pressing a button, turning on a light, signing in, signing out, opening the door, etc.) that sends data indicating, for example, the room identification, the type of activity to be conducted at that time in the room (e.g., karate class, etc.), user entry time, user exit time, etc. This transmitted data may be received, for example, by the module 502, interface 506, and/or electronic device 508 and stored. In some instances, the sensor included with the module 502 (if any) may be able to detect at least some data associated with these types of workouts, even if no machine is directly involved, such as information relating to step count, heart rate, pulse rate, cadence, accelerometer data, or other data. From this data, some features of or parameters relating to the workout may be derived, such as calorie burn, METs, speed, distance, etc., e.g., by the electronic device 508, interface device 506, and/or module 502, and this data and information may be stored. Even if no specific data relating to the workout can be detected by the module 502 (such as step count, heart rate, etc.), transmission of the room or locale identification data to the electronic device 508 (optionally through the module 502) can be useful to the user, e.g., to provide an indication and some record that a workout has taken place and optionally at least some data indicating the type of workout (which data and information may be entered into and included in the user's workout history).

Figure 8:
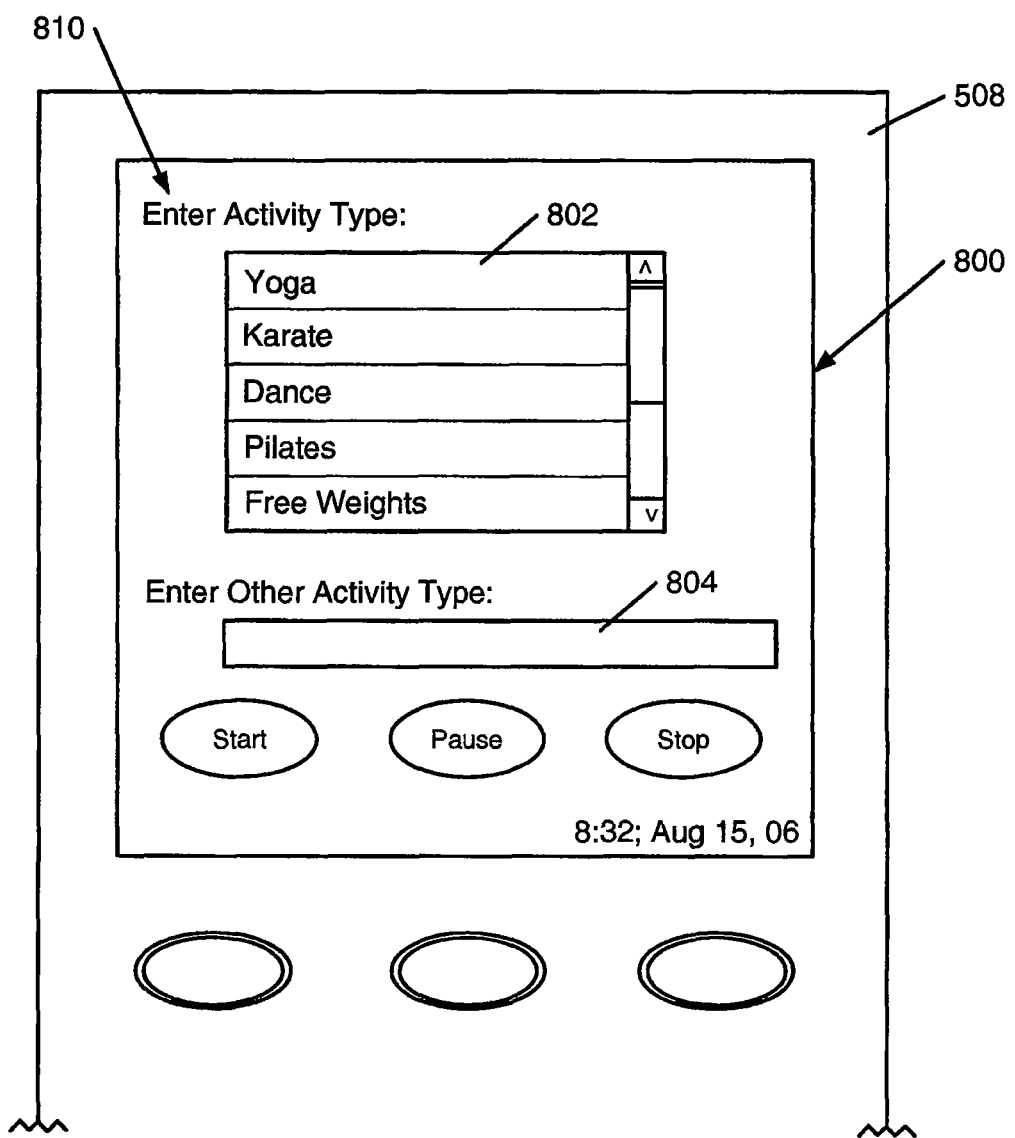
FIGS. 8-19 illustrate various example features that may be provided in and/or controlled by user interfaces of athletic performance sensing systems according to at least some examples of this invention.

Workout information can be entered into the electronic device 508 even in situations where there is no machine, room, or other locale 604 from which to transmit data and/or even in situations where the module 502 (or interface device 506 or electronic device 508) cannot sense data relating to the workout (e.g., when running, jogging, or walking outside; when participating in dance, aerobics, or other classes; martial arts training; free weight lifting; team sports (such as baseball, softball, basketball, football, soccer, etc.) etc.). The data may be provided, for example, by manually entering workout information into the electronic device 508. FIG. 8 shows an example of the electronic device 508 with a display screen 800 having an example user interface 810 allowing user input of information relating to a workout or activity in this situation. While a wide variety of information and combinations of different types of information may be entered, this example interface 810 includes a panel 802 through which the type of activity to be conducted may be selected from a listing and another panel 804 through which the type of activity may be entered (e.g., optionally activities not found in the panel 802). In addition, this user interface 810 includes "start," "stop," and "pause" buttons that allow users to record time and/or timing information associated with the workout or activity, if desired. Again, if the sensor included with the module 502 is able to detect at least some data associated with these types of workouts, such as step count, heart rate, pulse rate, or other data, this data may be collected, sent to the electronic device 508, stored, presented on display screen 800, and/or associated with the specific workout. Collection of data in this manner can be useful to provide at least some information for the user indicating his/her complete workout history (e.g., workout dates, attendance, workout lengths, etc.), even when little or no actual workout data from the available sensors can be produced or made available.

Also, any desired manner of inputting data into the interface screen 800 may be provided without departing from this invention, such as a keyboard, mouse, trackball, roller ball, stylus, pen, touch screen, touch pad, rotary input device, etc. Such interface systems and input devices are conventionally known and used in the electronic device art.

Of course, any desired data information or content may be requested and/or entered through the user interface 810 without departing from this invention. As more specific examples, data input can be requested and/or provided on a more granular level than that described above in conjunction with FIG. 8. For example, more detailed information regarding timing, duration, intensity, or other features of the activity may be requested via interface 810, e.g., depending on the activity type, user settings, etc. For example, if the selected activity was "Free Weights" or "Weight Training," the user interface 810 according to at least some examples of this invention may request entry of additional information, such as type of lifting performed (e.g., squats, dead lift, bench press, military press, curls, etc.); number of sets performed; number of repetitions per set; amount of weight lifted per set; etc. Additionally or alternatively, if desired, the weight machine and/or individual weights may include an electronic module (e.g., such as an accelerometer or the like for sensing direction changes and a transmission system (such as an RFID transmitter)) that allows automatic transmission of certain information to the electronic device 508 (optionally through the module 502 and/or interface device 506), such as repetition counters (each up/down movement of the weights), weight information per set, number of sets, etc. The transmission system may be activated automatically, manually, or semi-automatically.

Systems and methods according to examples of this invention may provide a wide variety of useful information, features, and/or data for users. For example, systems and methods according to examples of this invention allow users to store and retrieve data relating to one or more workouts, which may be stored, for example, on a local computer 702, the remote system 704, on portable devices 502, 506, and/or 508, etc. Any of the sensed data, timing information, and the like may be stored, retrieved, and further processed and analyzed by users. Systems and methods according to at least some examples of this invention further may allow users to compare their workout routines, data, and/or fitness level to other information, such as: their own stored workouts; stored workouts of other users of remote system 704 (optionally workouts of specific individuals, such as friends, workout partners, etc.; users of the same or similar size, weight, age, gender, fitness level, etc.; etc.); similar workouts of well known athletes or celebrities; and the like. As additional examples, if desired, systems and methods according to at least some examples of this invention may further allow users to compare their workout routines, data, and/or fitness level to information related to athletic events in which they may or may not have participated, such as road races, bicycling events, triathlons, etc. (e.g., "where would today's time have finished in last year's Marine Corps Marathon," "how do I compare with the speed of last year's Tour de France winner," etc.).

Systems and methods according to at least some examples of this invention also may be used to provide and/or suggest workouts for users (e.g., pre-programmed workouts, optionally taking into account various factors, such as user age, height, weight, fitness level, gender, past performance, goals, etc.). Such workouts may be designed by fitness experts, e.g., for individual users, for general categories or groups of users, etc. The workouts or information relating to the workout may be downloaded to the portable electronic device 508 (e.g., via computer 702, from remote system 704, etc.), and they may be designed to provide information to the user before the workout begins and/or as the workout progresses, optionally in real time. For example, the downloaded workout may provide a wide variety of information to the user, such as: real time workout parameter feedback (e.g., speed, distance covered, stair-stepping, elliptical, or other rate information, calories burned, elapsed time, etc.); workout activity or machine change information (e.g., when to move to a new machine or activity: "you are done on the treadmill, move to the stationary bike for 20 minutes;" machine setting change information (e.g., to be performed manually or automatically); etc.); real-time comparison information to previous workouts or to a user's "personal best;" etc.).

Moreover, the downloaded and/or presented information on electronic device 508 is not limited to workout information. The electronic device 508 also can provide warnings or reminders (e.g., proper warm-up or cool-down reminders, particularly when abrupt changes in activity are sensed (e.g., by module 502), etc.; over-training warnings (e.g., by comparing workouts on consecutive or recent dates); nutritional reminders; etc). Also, because systems and methods according to at least some examples of the invention can store information regarding workouts performed by a user over time, they can recognize a user's preferences and provide customized workouts or suggest certain workouts or portions thereof, so that the user's workout routine will change (to help prevent boredom) and help him/her better accomplish their goals. Systems and methods according to at least some examples of this invention may be programmed and adapted to provide user rewards over time, e.g., based on continued usage, attaining pre-set goals, etc. Any type of reward may be provided, such as presents, prizes, coupons, discounts, motivational audio or video content, etc., as will be described in more detail below.

Because at least some portions of systems and methods according to examples of this invention may receive data from multiple users, users can compete against one another and/or otherwise compare their athletic performances, even when the users are not physically located in the same area and/or are not competing at the same time (e.g., virtual races or competitions). These features can help motivate users and keep their workout routines interesting. Moreover, systems and methods according to at least some examples of this invention can suggest new workout programs to a user based on workout programs followed by other users (whether or not the "other users" are known by the original user), optionally programs followed or practiced by other users of similar size, weight, or age; the same gender; the same general fitness level; etc. Such features can motivate users to compete with and/or beat their friends or other users at various different workout routines. Changing workout routines also can help users more quickly improve, reach their goals, break through "plateaus," etc.

While various aspects of the invention described in this sub-section are described as providing data and information to/from the portable electronic device 508, those skilled in art will recognize that the data and information may be transmitted to/from other devices without departing from this invention, such as the module 502, the interface device 506, a user's PC or other input device or exercise equipment 604 or 702, etc.

Figure 9:
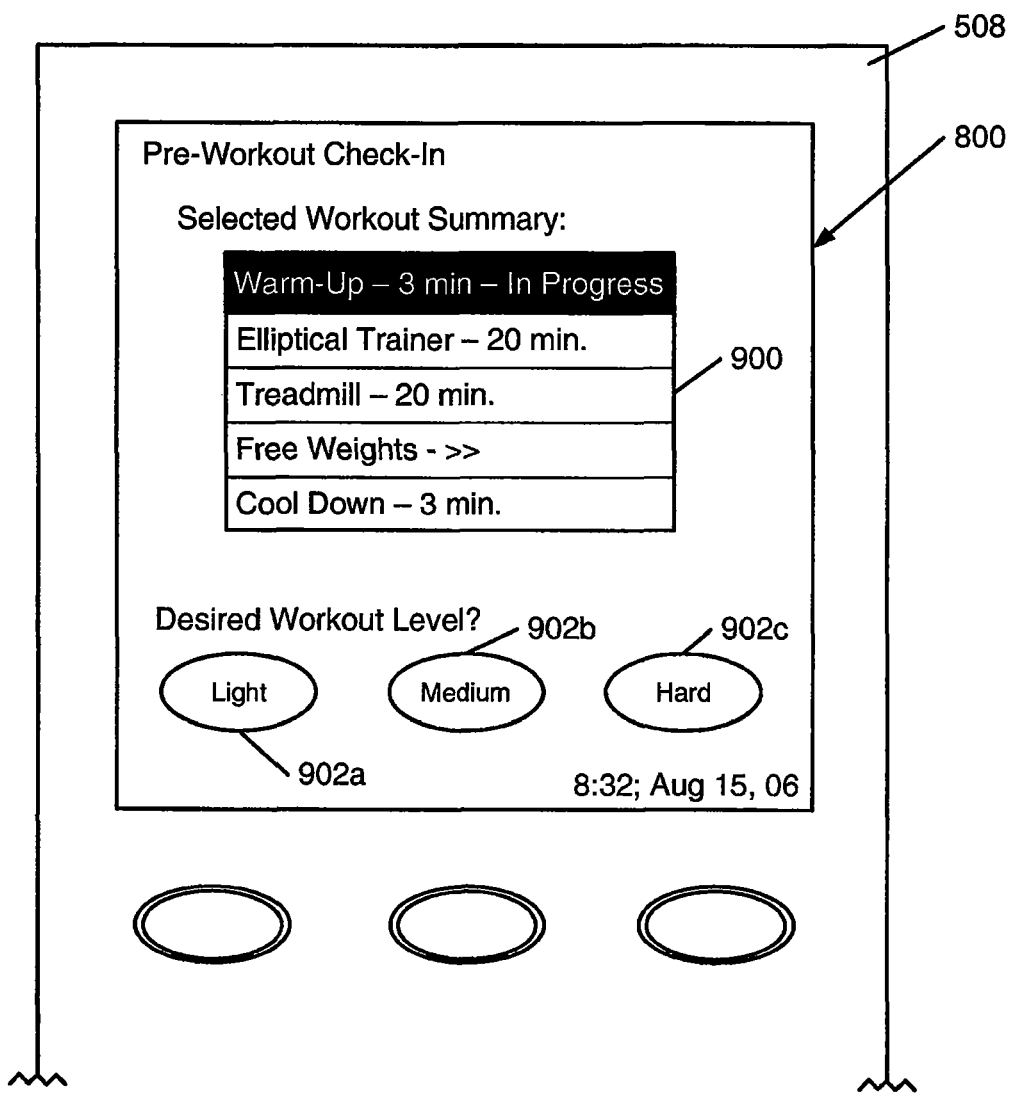

D. Use of Subjective User Input and/or Feedback in Systems and Methods According to Examples of this Invention Systems and methods according to at least some examples of this invention utilize user feedback or user input in various ways, e.g., to better customize workouts; to change or improve the workout entertainment and/or motivational content; to maintain workout "freshness;" etc. FIG. 9 illustrates one example of systems and methods in accordance with this invention in which user feedback is used to select one or more features of a workout before it begins and/or at the early stages of the workout routine. As shown, in this example, the screen 800 of electronic device 508 displays the general features of a selected workout (e.g., the individual workout activities) for that workout session in panel 900. At some time toward the beginning of the workout (e.g., either before actually starting, during, or after an initial warm-up period, etc.), the user is prompted to enter information indicating how he or she "feels" that day. More specifically, in this illustrated example, as the warm-up period begins or progresses (as indicated by the darkened time slot in the workout schedule shown in display panel 900), the system and method of this example ask the user to input information regarding the desired workout level for that day (e.g., input buttons 902a, 902b, and 902c are provided allowing a user to indicate whether a "light," "medium," or "hard" workout, respectively, is desired for that day). Any number of potential choices for the workout level may be provided without departing from this invention. Optionally, this user interface may be displayed to the user along with motivational, coaching, and/or warning media content, as will be described in more detail below (e.g., audio content encouraging the user to select a hard workout level, a reminder of the past workout, etc.).

The characteristics or parameters of the workout may be varied widely, depending at least in part on the selected workout level. For example, if desired, the types of activities included as part of the workout may be changed, depending on the selected workout level. As another example, the time duration(s) of one or more of the activities may be changed, depending on the selected workout level. As yet another example, if desired, one or more of the amount of resistance, timing/pace/distance goals, calorie burn goals, overall workout times, incline levels, number of free weight lifting sets, number of repetitions per set, free weight lifting weight levels, and the like, may be varied to increase or decrease the "workout level." Also, various combinations of the potential changes described above (as well as other potential changes) may be used to change the "workout level" for the user based, at least in part, on the user's input regarding the desired workout level. Also, any desired amount of increase or decrease in the workout level may be made without departing from this invention. If desired, systems and methods according to this example of the invention may allow more detailed user input indicating the workout level parameters, including user input selecting the various parameters or goals for individual activities and/or the overall workout.

If desired, systems and methods according to at least some examples of this invention may allow users to "drill down" to view (and potentially change) more information regarding a particular workout or activity. For example, if desired, the user could one of the identified workout activities (e.g., treadmill), which action could open another user interface/input panel identifying additional information regarding that activity (e.g., treadmill speed, treadmill incline, treadmill pre-set program information, etc.). If desired, the user may be able to modify more detailed aspects of an individual workout or activity, e.g., through such additional user interface/input panels or in other manners. Any desired number of "drill down" panels and/or levels for accepting user input may be provided without departing from this invention.

Selection and/or modification of a user workout based on subjective user input are not limited to the pre-workout, pre-warm-up, and/or early workout stages. Rather, systems and methods according to some examples of this invention may periodically prompt users to indicate how they "feel" and/or to indicate whether the workout parameters should be changed in some manner. These prompts may occur automatically at various different times during a workout or activity, e.g., at predetermined intervals; at predetermined times into a workout or activity; when the system senses excessive user difficulty in "keeping up" with the workout; when the system senses that the user is too easily keeping up with the workout (e.g., based on pulse or heart rate data, etc.); when a user potentially could exceed his/her personal best, reach a goal or milestone, etc.; etc. Such features can help motivate users and help them more quickly increase their fitness level and/or reach their fitness goals while helping to avoid soreness and overtraining (and potentially discouraging) the user.

Figure 10:
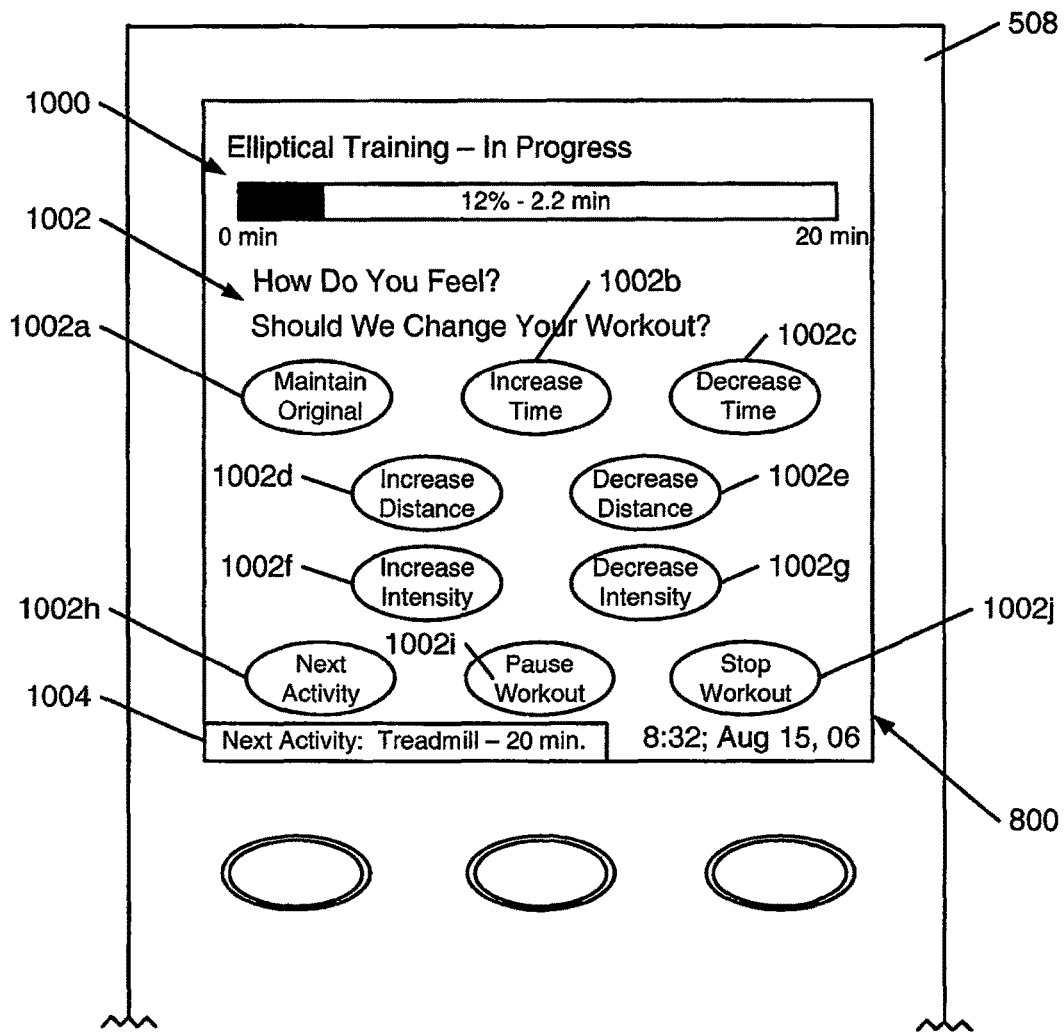

FIG. 10 illustrates an example of the display screen 800 of electronic device 508 providing an example user interface in which the user is prompted to provide feedback during the course of a workout activity. As shown, progress panel 1000 shows the user their current workout activity (elliptical training in this example) and the degree to which this activity has been completed (12% completed, in this example). At this time in this example workout, the system has prompted the user for their subjective feedback (area 1002), asking the user whether the workout should be changed. In this illustrated example, the user interface area 1002 provides input buttons indicating several options for the user, namely: maintaining the original workout activity parameters 1002a; increasing the workout activity time goal 1002b; decreasing the workout activity time goal 1002c; increasing the workout activity distance goal 1002d; decreasing the workout activity distance goal 1002e; increasing the workout activity intensity 1002f; decreasing the workout activity intensity 1002g; changing to the next activity 1002h in the selected workout routine (the next type of activity is indicated in the interface area 1004 as a "treadmill" workout activity); pausing the workout 1002i; or stopping the workout 1002j. Any desired information, change options, and the like may be included in the user interface area 1002 and/or information like that described above may be made available through plural input screens without departing from this invention. Also, if desired, this user interface screen may be presented with appropriate motivational, coaching, and/or warning information (e.g., an audio or video clip encouraging the user to increase his/her level, etc.).

Figure 11:
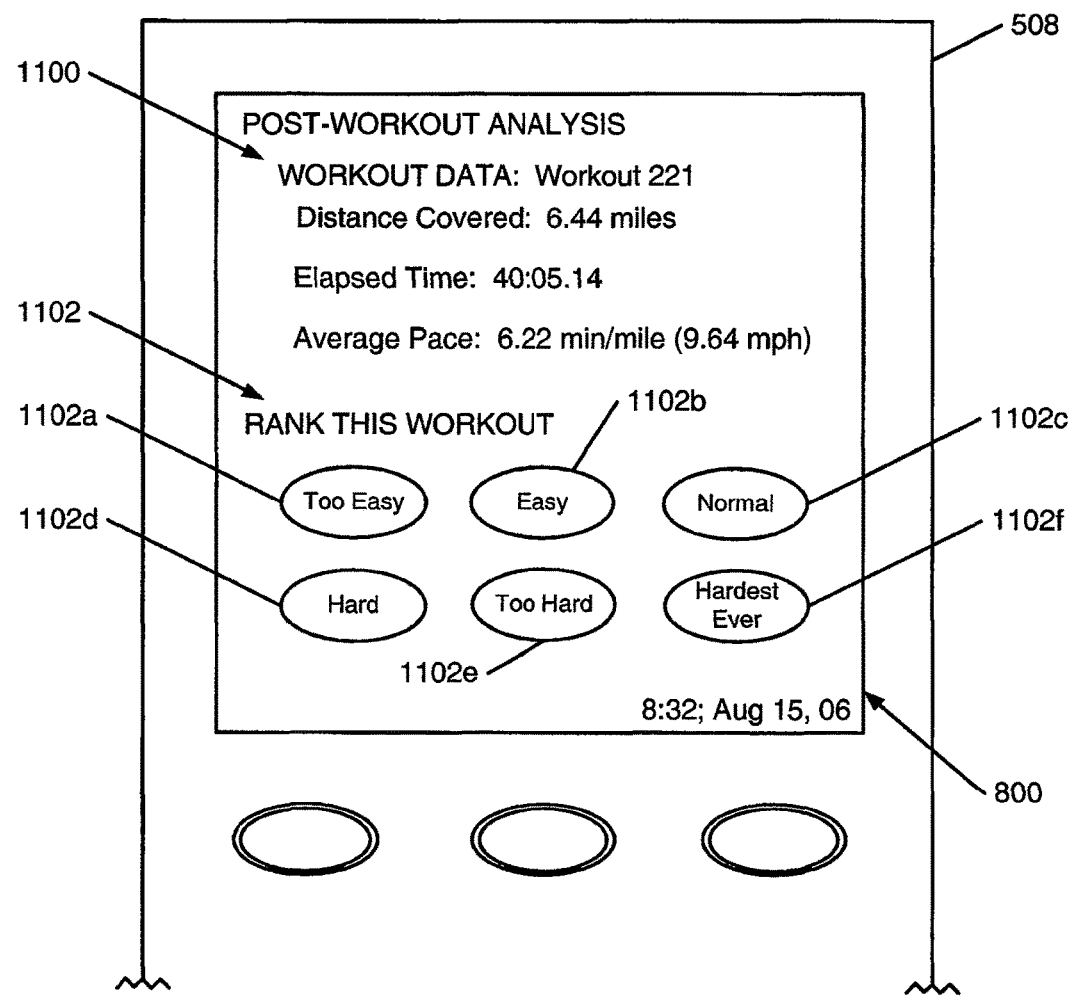
Figure 12:
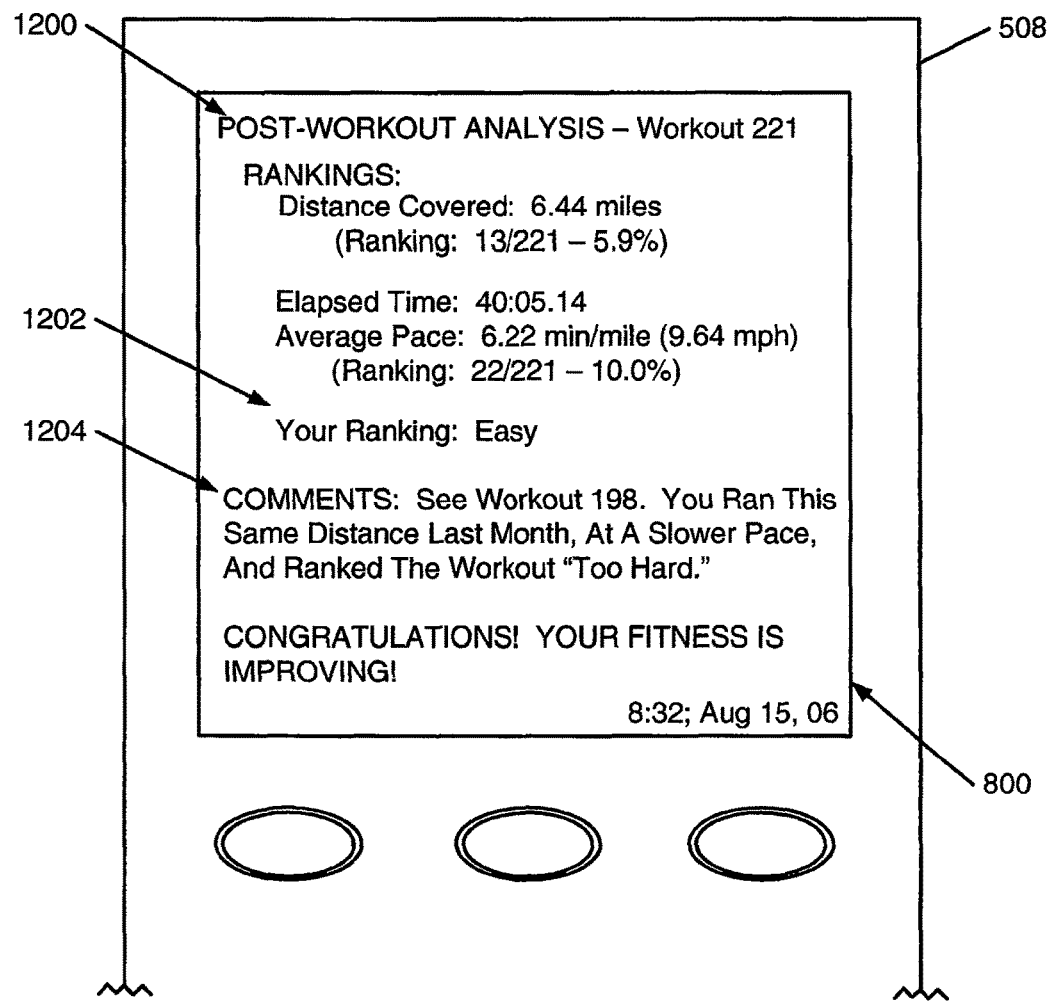

Subjective user input also may be received and used by systems and methods according to at least some examples of this invention after the workout is completed. FIGS. 11 and 12 illustrate examples of user interface screens that may be used in post-workout analysis situations. For example, as shown in FIG. 11, once a workout is completed, systems and methods according to at least some examples of this invention may be programmed and adapted to provide workout information to the user on display screen 800. In this illustrated example, a workout summary area 1100 is provided, indicating various features of the workout, such as: a workout identification code ("Workout 221" in this example); "distance covered" data; "elapsed time" data; and "average pace" data. Any type of data or information may be provided in the workout summary area 1100 without departing from this invention, including user physical or physiological data, etc. Additionally, if desired, workout summary data may be provided for each individual activity or segment included in the workout (e.g., treadmill, elliptical training, weight-lifting, etc.), and the type of data provided for the various different activities may be the same or different (e.g., workout summary data may be different for treadmill workouts as compared with other workouts, such as stationary bicycle, elliptical training, stair-stepping machines, outdoor running, rowing, etc.). Scroll bars, additional display screens, and/or other ways of providing additional information in workout summary area 1100 may be provided in order to allow inclusion and/or presentation of information beyond that which will fit within area 1100 on the electronic device 508.

FIG. 11 further shows a subjective user input area 1102 on the display screen 800 associated with this post-workout analysis. More specifically, systems and methods according to this example of the invention request that the user "rank this workout" using subjective user input area 1102. While any desired rankings and/or potential options may be made available for the subjective user rankings without departing from this invention, in this illustrated example, the user has six choices for ranking the workout, namely: "too easy" 1102a, "easy" 1102b, "normal" 1102c, "hard" 1102d, "too hard" 1102e, and "hardest ever" 1102f. Advantageously, in at least some examples of systems and methods according to this invention, this subjective ranking capability (e.g., ranking area 1102) will be provided to the user on the portable, user carried electronic device 508 immediately upon completion of the workout, so that the true subjective feel and effects of the workout are immediately fresh on the user's mind.

The subjective data may be used in a variety of ways by systems and methods according to examples of this invention. For example, once a subjective user ranking is received in the ranking area 1102 of FIG. 11, an additional post-workout analysis screen 1200 (e.g., as illustrated in FIG. 12) may be provided. This post-workout analysis screen 1200 uses the subjective ranking information and compares the actual parameters of the present workout with objective historical data relating to the same or similar workouts in order to provide feedback to the user regarding this workout, their fitness level, and/or their progress in reaching a pre-set goal. As shown in FIG. 12, in this example, the user ranked the workout as "easy" (area 1202). The post-workout analysis of systems and methods according to this example of the invention compares this workout to other workouts. While any desired parameters may be compared, in this illustrated example, the objective overall distance covered and average pace data for the present workout were compared and ranked with the objective data from previous workouts (optionally, from workouts having the same or similar conditions and/or parameters, workouts including at least some of the same activities, etc.). Additionally, in this example, the subjective user data was used to provide feedback (in the form of "Comments" in area 1204) indicating how the subjective ranking of this workout compares to earlier workouts. Any type of commentary and/or other information may be provided in area 1204 (or in some other manner, such as via audio, via email, etc.), e.g., coaching feedback; motivational or congratulatory feedback; reward information (e.g., a coupon or code for receiving a discount on athletic equipment or clothing, etc.); etc. The subjective feedback also may be used by systems and methods according to at least some examples of this invention to automatically modify future workouts for users, e.g., increase one or more workout parameters (e.g., distance goals, time goals, intensity or resistance level settings, etc.) for workouts indicated as "easy" or "too easy," decrease one or more workout parameters for workouts indicated as "too hard" or "hardest ever," and/or to otherwise modify workouts so as to continue challenging and motivating users while preventing overtraining, soreness, discouragement, etc.

Comparison of subjective and/or objective workout data is not limited to comparisons with efforts made by the individual user and/or historical data generated by the individual user. As described above in conjunction with FIG. 7, systems and methods according to at least some examples of this invention may communicate with remote systems (e.g., over the internet or other network connection), and multiple users may send their workout data to the same remote system(s). Therefore, the user input subjective data, as well as the objective data, relating to a user's workouts may be compared to workout data and/or subjective input generated by others. In this manner, the systems, methods, and/or users can compare their workouts and fitness to other users, such as specific individuals (e.g., their friends, relatives, etc.); famous athletes or celebrities; other users of similar body type or other characteristics (e.g., the same gender; the same or similar age, height, weight; the same general fitness level; etc.); etc. Also, systems and methods according to some examples of this invention may provide completely new workouts for an individual, e.g., based on the user's subjective workout feedback; "borrowing" workouts of others saved in the system (e.g., people performing similar workouts, people of similar age, height, weight, fitness level, etc.); etc. Multiple users may participate in virtual races or other fitness competitions (e.g., first to run 100 miles, first to lift 5000 lbs., etc.), which can help keep users motivated and improve their fitness. Such virtual races or competitions also may be designed to have a charitable beneficiary, e.g., in which users obtain pledges for monetary support for every mile run, or the like, akin to actual (non-virtual) road races used to raise money for charity.

E. Use of Music and Other Content in Systems and Methods According to Examples of this Invention Aspects of this invention further relate to the use of music and/or other audio and/or video content in athletic performance sensing and/or tracking systems. Such content may be useful in a variety of ways in systems and methods according to examples of this invention, e.g., for providing entertainment, information, coaching tips or reminders, motivational content, etc. Advantageously, in accordance with at least some examples of this invention, in addition to being able to download workout routines and/or data as described above, electronic device 508 will constitute or include an audio and/or video presentation device that allows users to also play and/or download music, videos, or other audio/video data for presentation during the course of a workout (e.g., a radio, a tape player, an MP3 player, an IPOD® device (commercially available from Apple Computer, Inc., of Cupertino, Calif.), etc.).

While the audio or video presentation device may be used in a conventional manner, e.g., with user controlled content and/or output during the course of a workout, systems and methods according to at least some examples of this invention allow more user interaction and control over the content presentation provided during the workout. For example, systems and methods according to at least some examples of the invention may allow users to pre-program and/or "mix" their own workout with audio/video and/or other content, e.g., to include desired audio/video content (e.g., music playback, video playback, coaching or motivational content, etc.) at desired times and in a desired timing or relationship with respect to various different phases of a workout routine or exercise program. Plural workout routines, optionally user mixed workout routines, stored and downloaded workout routines (optionally including pre-selected or user selected music), purchased workout routines (optionally including pre-selected or user selected music), and the like, may be stored on or downloaded to the electronic device 508. Also, in systems and methods that utilize an output device, a networked connection, or other computer base station or remote station, users may make their pre-programmed workouts available to others (e.g., "publicly available" or otherwise selectively available to one or more other individuals on the system), e.g., for downloading over the network or otherwise transmitting to another user's electronic device 508.

Figure 13:
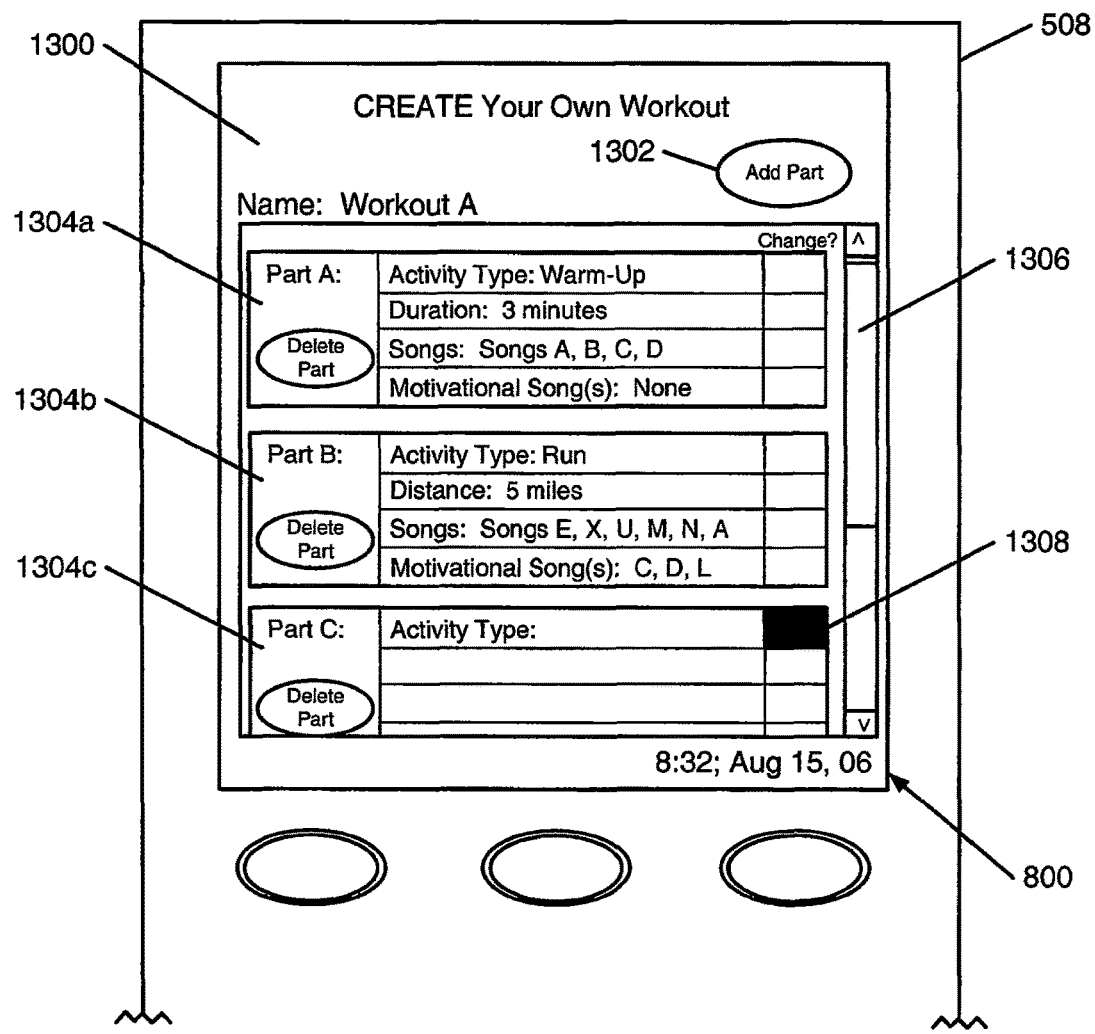
Figure 14:
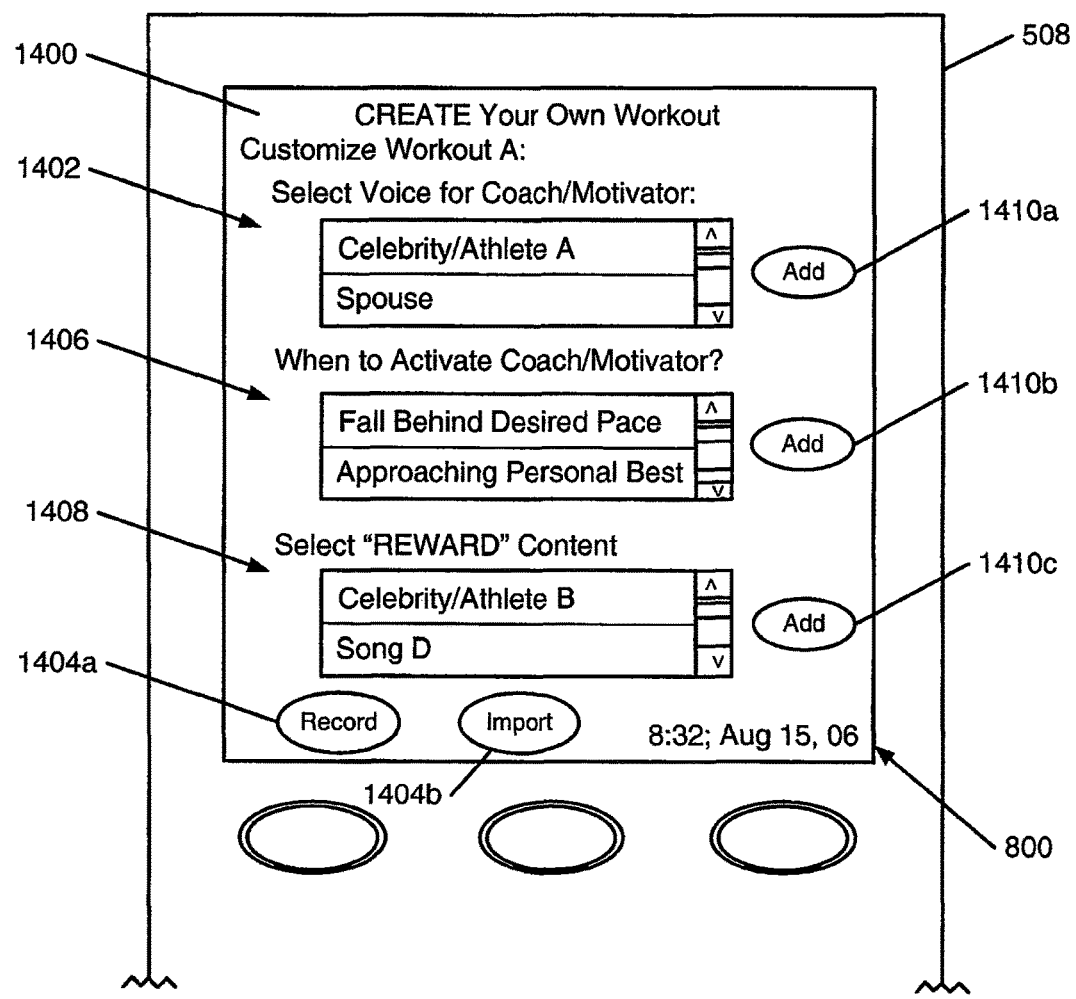

FIGS. 13 and 14 illustrate example features of user interfaces that may be used to allow users (or others, such as coaches, trainers, etc.) to create their own customized workout routines (e.g., for their own use, for use by others, etc.). While these figures illustrate providing the user interface and creating a workout routine using electronic device 508 for user input, those skilled in the art will understand that any computer in communication with the overall system (e.g., via the internet, via a wired connection, etc.) may be used for creating the workout routine without departing from this invention, such as personal computer 702 and/or another computer in communication with the electronic device 508 and/or remote system 704 from FIG. 7. Also, while particular user interface elements are shown and described in conjunction with FIGS. 13 and 14 (e.g., scroll bars, input regions, etc.), other user interface elements, user input hardware, and/or ways for receiving user input to create and/or change features of the workout routine may be used without departing from the invention.

User created workout routines according to examples of this invention may include one or more "parts," wherein a "part" constitutes a specific type of workout activity, such as: warm-up, walking, running, biking, rowing, use of exercise equipment or gym machines (such as treadmills, stair-stepping machines, elliptical machines, exercise bicycles, rowing machines, cross-country ski simulators, etc.), weight lifting (free weights or gym machines), yoga, dance, aerobics, martial arts, team sports, cool-down, etc. In this example system and user interface, any combination of activities may be included in a workout routine without departing from this invention, including, for example, gym or spa based activities, outdoor or free range activities, machine or free (non-machine) based activities, team sports or individual activities, etc.

In accordance with examples of this invention, as illustrated in FIG. 13, a user can begin creating a workout by selecting the "Add Part" button 1302 on user interface 1300, to add a distinct "part" or activity to the workout routine. In this example system and interface, adding a "part" or activity to the workout routine creates a "part" or activity block 1304a, 1304b, and 1304c. While three activity blocks 1304a, 1304b, and 1304c are illustrated in FIG. 13, any number of activity blocks may be included in a workout routine, and other blocks relating to the workout routine may be viewed, for example, by interacting with scroll bar 1306 or otherwise indicating a desire to see other parts of the workout routine.

Once a part or activity block is created, it may initially appear blank or with a line for the "activity type" provided (see "Part C" in activity block 1304c in FIG. 13). A user then may select the desired activity type. For example, as indicated in FIG. 13, after adding the part or activity block 1304c, in this example interface 1300, the user may indicate a desire to add or change the "activity type" by selecting the "change" block 1308 associated with the Part C "Activity Type" line. This action may cause a list of possible "activities" to appear (e.g., as a "pop-up," as a separate screen, as an overlay, etc.), and the user may select the desired activity for the workout from the list, e.g., using any of a variety of user interface elements and interaction mechanisms and methods, as are known and used in the art.

After the activity type is selected, other lines of the activity block may be filled in, optionally in a user changeable manner. The selected activity type may affect the data or information to be filled in and/or included in the remainder of the input lines for the "part" or activity. For example, selection of an activity type that utilizes an exercise machine may populate other lines of the part 1304a, 1304b, and/or 1304c to include information relevant to that machine, such as desired speed, desired incline level, desired weight or other resistance levels, other desired workout intensity features, desired distance, desired calorie burn, desired distance traveled, desired total elapsed time, desired machine settings (such as hill, random, etc.), etc. If desired, systems and methods according to at least some examples of this invention may allow users to even more finely customize the workout routine, e.g., by providing the ability to control and/or change the desired parameters of a workout over time during a given activity (e.g., change hill, resistance, or intensity levels of a machine over time, change running speed over time, etc.). While the additional lines of a given "Part" 1304a, 1304b, and/or 1304c may be populated with default settings, e.g., when the part and/or activity type are/is initially selected, systems and methods according to at least some examples of the invention may allow users or others to freely customize and/or change the content of these lines, e.g., in any desired manner, including, if desired, in the general manners described above for changing the "activity type." Optionally, if desired, the default settings, if any, may be determined based on any desired information, including, for example, historical data relating to a user's recorded workout history in general, a user's workout history for that particular activity type, or other features of a user's preferences or history (such as typical overall workout elapsed time, elapsed distance, typical speed, typical incline or resistance settings, weight, age, weight loss/gain, etc.).

As illustrated in FIG. 13, data input creating and relating to the various workout parts 1304a, 1304b, and 1304c includes "Songs" (or optionally other media or other content) that may be presented to the user during the course of that part of the workout. When the electronic device 508 is a media playback device (such as an MP3 player, an IPOD® 0 device (commercially available from Apple Computer, Inc., of Cupertino, Calif.), etc.), systems and methods according to at least some examples of this invention may play the user indicated list of songs during that part of the workout routine. If desired, song or other media content presentation can be even more specifically targeted to specific times or portions of the workout activity. In these manners, users can selectively and easily control the media content presented during various portions of the workout routine and activities without the need to adjust the settings or output of the device 508 during the course of the workout.

A variety of ways of presenting the media content may be provided without departing from this invention. For example, if desired, systems and methods according to at least some examples of this invention may play back the user indicated songs in the user specified order, in a random or shuffled order, in a continuous looping order, etc. Additionally or alternatively, if desired, the user may include media content in the list or line for that part 1304a, 1304b, or 1304c that will last longer than the allotted time or duration for the activity, and systems and methods according to the invention can be adapted to handle this situation in any desired manner (e.g., by stopping the playback when the activity ends or changes, and optionally resuming the playback from the stopped location or from the interrupted song the next time that workout activity, workout part 1304a, 1304b, or 1304c, or media content list is used, etc.). As yet another potential option, if desired, playback may continue until the next workout activity is undertaken (e.g., as indicated or sensed by module 502, user input, etc.), to continue providing entertainment and/or other content to the user between workout activities. Other desired ways of handling these situations may be used without departing from this invention. Also, if desired, a user may be provided with the ability to override the pre-selected content with new media selections during the course of the workout.

If insufficient media content is specified for an activity's duration, systems and methods according to examples of the invention also may handle this situation in any desired manner without departing from this invention. For example, the specified songs or content may be repeated, new songs or content may be automatically selected (optionally, based on other user input or history, such as from user enumerated "favorites," from most frequently played content, from content with similar characteristic(s) to the user identified content (e.g., content with a similar beat, cadence, etc.; content from the same artist or the same genre; content "borrowed" from other user workouts including this same activity; content "borrowed" from other workout activities within this same workout; etc.). Other desired ways of handling these situations may be used without departing from this invention.

The workout parts 1304a, 1304b, or 1304c of this illustrated example include another feature, namely, a "Motivational Song(s)" line. If desired, users of systems and methods according to at least some examples of this invention may select one or more "motivational songs." The motivational song(s) (or other audio/video media content) may be played at various times during a workout routine, e.g., in an effort to help motivate the user to better or continued performance. For example, when a user of a gym machine approaches a portion of the workout having high intensity (such as high incline, high resistance level, increased speed, etc.), systems and methods according to at least some examples of this invention may automatically output one of the motivational songs (or other media content), in an effort to motivate the user to expend additional effort to meet the additional increased intensity challenge. As additional examples, motivational song(s) may be automatically triggered, for example: when a user approaches a personal best (e.g., best split time, best mile time, longest total distance, etc.); when the user approaches a predetermined time, distance, or location in the workout; when the user falls behind a predetermined pace; when the user approaches a preselected goal or milestone; etc. Any desired time, timing, or other parameters may be used for triggering presentation of the motivational content without departing from this invention (examples of which will be described in more detail below). The motivational content also may include alphanumeric or textual information (e.g., in addition to or in place of audio and/or video content).

As yet another example, if desired, the device 508 (or 506) may include a "motivate" hard button, the user interface may include a "motivate" icon, or the overall system otherwise may make presentation of the motivational content readily available for the user to manually trigger during the workout routine, so that users can easily trigger presentation of motivational songs or other content at will (e.g., if they begin feeling lethargic or otherwise feel they are unmotivated or falling behind their desired output or pace, if they simply decide they want to pick up the pace or need motivation, etc.).

FIG. 14 illustrates additional potential features that may be available for customizing and mixing workouts for users of systems and methods according to at least some examples of this invention. In addition to or as an alternative to the motivational song(s) features described above, systems and methods according to at least some examples of this invention may allow users (or others) to select an audio/video "coach" or other "motivator," if desired, to provide encouragement to the user before the workout, as the workout progresses, and/or after the workout. This content source may be selected, for example, using user interface area 1402 of the interface 1400 shown in FIG. 14 ("add" button 1410a allows the user to select one or more of the available options for use as the coach/motivator voice, video, etc.). Any desired audio/video content may be used without departing from this invention, including, for example, voices or video of: a user's coach or trainer; a famous athlete or celebrity (e.g., selected by the user, optionally from external sources, such as the remote source 704 described above in conjunction with FIG. 7; stored in memory on electronic device 508; etc.); a user's spouse; a user's child; the user; etc. If desired, the user interface 1400 also may include user interaction and/or input elements, such as icons or buttons 1404a and 1404b, that allow users to record or import (from an external source, such as remote source 704 over a network of FIG. 7) any desired audio and/or video content to be used as the coach or motivator content (e.g., the user's child's voice encouraging the parent to really try hard for a strong finish, etc.).

As exemplified by area 1406 of the user interface 1400 of FIG. 14, a wide variety of options and/or situations may be made available for automatically triggering or activating the coach/motivator content. Any number of different trigger events or situations may be selected by a user and used in a given workout routine or activity without departing from the invention (optionally with some delay between successive activations of the coach/motivator content, e.g., to give the user an opportunity to put forth the additional effort in response to the previous coach/motivator content, to prevent overplaying of the content, etc.). One or more of the user desired triggers may be selected, for example, using "add" button 1410b. Also, different workouts or parts thereof may include and use different trigger or activation events, optionally, events selected and determined by the user. Examples of potential triggers for coach/motivator content include: falling behind a predetermined pace (e.g., slowing below an actual trigger pace level, slowing a certain percentage below a base or average pace, etc.); approaching a personal best (or a personal worst); working out for a predetermined elapsed time; reaching a predetermined distance or location; reaching a predetermined number of sets or repetitions; approaching a difficult or intense portion of the workout; falling pulse or heart rate; etc. Also, if desired, systems and methods according to at least some examples of this invention may have automatic or default triggers, optionally triggers that activate in addition to user selected activation triggers. The system need not be designed to trigger coach or motivator content during each triggering event experience, e.g., if doing so would result in over exposure to the coach/motivator content.

If desired, systems and methods according to at least some examples of this invention additionally or alternatively may include and present "reward content" to users. Users may enter and/or control the reward content through area 1408 of this example user interface 1400. Reward content may take on a variety of different forms without departing from this invention, such as an audio and/or video congratulatory statement from a celebrity, famous athlete, spouse, child, coach, trainer, etc. (e.g., similar to the sources of coaching/motivational content described above). Additionally or alternatively, if desired, the reward content may constitute a reward song, e.g., selected by the user, selected from a predetermined list created by the user, etc Like the coach/motivator content selected through the use of interface area 1402, the content source for the reward content may be selected using any desired user interface system or elements, for example, the "add" button 1410c, which allows selection of one or more available options for reward content from a listing. The reward content may originate from any desired source, such as from external sources, like a remote source 704 described above in conjunction with FIG. 7; stored in memory on electronic device 508; etc. If desired, user interaction elements, such as icons or buttons 1404a and 1404b also may be used to record or import (from an external source, such as remote source 704 over a network of FIG. 7) any desired audio and/or video (or other) content to be used as the reward content. Although not illustrated in FIG. 14, the user interface 1400 also may accept user input to indicate the times and/or triggers for activating the reward content, e.g., for achievement of any type of goal (e.g., running a lap or split time or distance at or faster than a certain pace; increasing the number of weights, sets, or repetitions when weight lifting; increasing incline or resistance levels on exercise machines; increasing total elapsed time or distance in an activity; successfully achieving a goal indicated by the coach or motivator; etc.). For example, an area similar to area 1406 for triggering the coach/motivator content may be used for specifying user selected reward triggers.

While reward content may be presented at the end of a workout or activity, this is not a requirement. Rather, if desired, reward content may be presented at any relevant time during an athletic performance, e.g., for achievement of any type of goal or milestone (e.g., running a lap or split time or distance at or faster than a certain pace; increasing the number of weights, sets, or repetitions when weight lifting; increasing incline or resistance levels on exercise machines; increasing total elapsed time or distance in an activity; etc.). Presenting reward content at various intermediate time periods can serve a dual purpose of additionally providing motivational content to the user. Reward content also may constitute alphanumeric or textual content (e.g., in addition to or in place of audio and/or video content).

Figure 15:
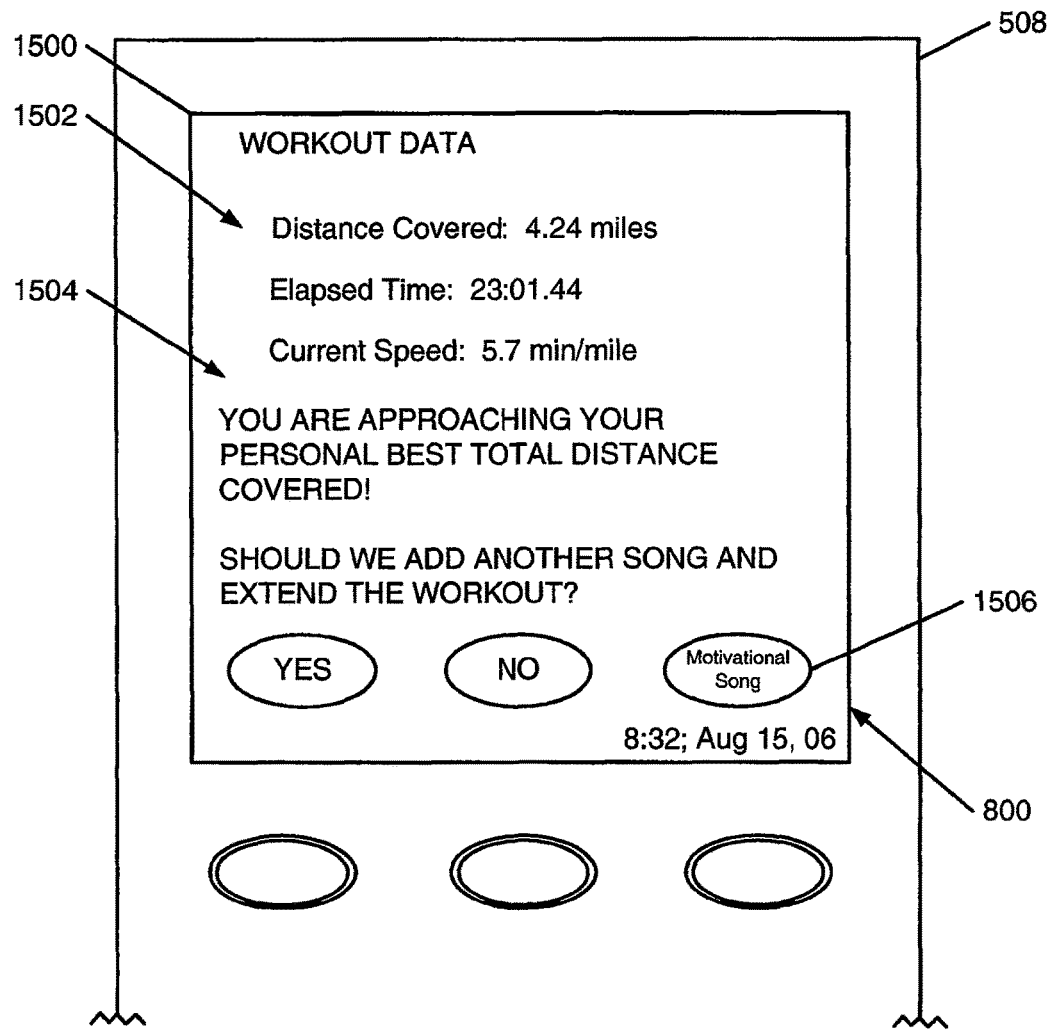

FIG. 15 illustrates an example of use of the display screen 800 of an electronic device 508 for providing a user interface 1500 including motivational content, e.g., to help motivate users to extend their workout, to improve their performance, and/or to attain or exceed their desired fitness goals or personal bests. As a workout routine proceeds in this example system and method, the electronic device 508 receives speed, distance, and timing information and compares this information to past workout data for the user relating to his/her personal bests. In this illustrated example, total distance, elapsed time, and current speed data are displayed to the user in area 1502. In addition, the collected data relating to the existing workout in this example indicates that the user was approaching his/her personal best in total distance covered. Any relevant data may be used to trigger this type of motivational content (e.g., total time, total calorie burn, current pace, etc.).

In such situations, systems and methods according to at least some examples of this invention may prompt the user to increase his/her effort and/or extend his/her workout in an effort to reach a predetermined goal or milestone and/or to set a personal best. Users may be informed of the presence of this prompt on the screen, if desired, using an audio and/or visual indicator, such as a beep, a flashing light or icon, etc. Various types of potential motivational content are described above in conjunction with FIG. 14. Additionally or alternatively, if desired, music (or other audio, video, textual, or alphanumeric content) may be used as a motivator. In the illustrated example, area 1504 of the interface 1500 advises the user that he/she is approaching some goal or milestone. The interface 1500 then encourages the user to extend the workout, e.g., for the length of time represented by at least one additional song. If the user indicates "yes" in response to this prompt, one or more additional songs will be played and the workout may be extended (if "no" is indicated, the workout may continue and end at its originally designated time/distance, etc.). Interfaces of the types illustrated in FIG. 15 may be particularly useful in situation where achieving the identified goal, milestone, or personal best will extend the workout in some manner beyond previously user set workout parameters (e.g., extend the overall time, distance, etc.), e.g., to give the user an opportunity to maintain his/her original schedule, if desired.

FIG. 15 illustrates an additional potential option that may be available in such situations. Rather than simply playing the next song from a listing or randomly selecting a song from those stored on or available through the electronic device 508, systems and methods according to at least some examples of this invention may allow users to designate use of and/or select one of their particularly identified motivational songs during this extended workout period. This may be accomplished, for example, by selecting the "motivational song" icon 1506. This action may automatically select a song from the user's pre-designated motivational song listing (e.g., see FIG. 13), optionally a random selection from that listing, if the motivational song listing includes multiple songs. Alternatively, if desired, interaction with icon 1506 may activate a listing that allows the user to select a specific motivational song desired at that time. Other interfaces and ways of providing a motivational song to the user may be used without departing from this invention.

The motivational song icon or button (or other interface element) 1506 may appear in some or even all screens of the overall systems, methods, and user interfaces according to examples of this invention, if desired. This feature can allow users to have easy access to and activation of motivational content. Additionally or alternatively, if desired, a hard button or other hardware element may be provided with the electronic device 508 (or interface 506 or other device) to allow easy access to and/or activation of the user's motivational content.

Additional examples of user interfaces relating to, features of, and use of motivational songs and motivational song libraries will be described in more detail below in conjunction with FIGS. 16-19.

F. Use of Subjective User Input Relating to Music and/or Other Content in Systems and Methods According to Examples of this Invention As described above, e.g., in conjunction with FIGS. 13-15, one aspect of systems and methods according to at least some examples of this invention relates to providing entertainment, motivational, and/or reward content (e.g., audio, video, or other media content, alphanumeric or textual content, etc.) to users, e.g., in an effort to keep users from becoming bored and/or to drive users to improve their fitness, achieve their goals, etc. Motivational songs (or other media content) may be used at a variety of different times during a workout, such as when a user has an opportunity to reach a pre-selected goal or milestone; when a user has an opportunity to reach a personal best; when a user actually achieves a goal, reaches a milestone, or sets a personal best; when a user falls behind a pre-selected pace or goal; when a user requests a motivational song; etc.

Figure 16:
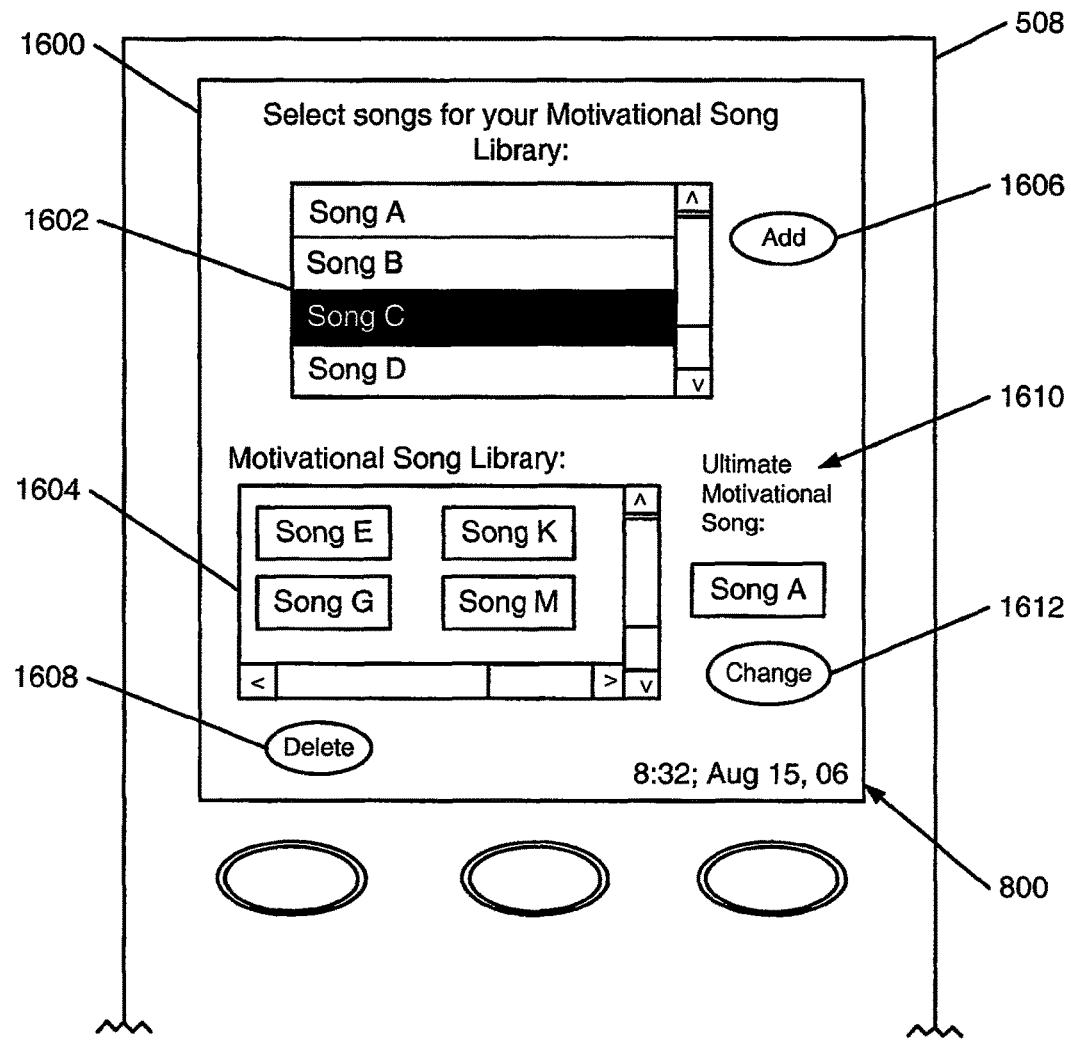

FIG. 16 illustrates an example user interface 1600 through which motivational songs may be selected by users based on their own personal preferences. This user interface 1600 may be made available to users at any desired location, e.g., provided on the electronic device 508, provided on a user's personal computer 702, downloaded from a remote system or source 704, etc. In this illustrated example user interface 1600, activation of the interface 1600 produces a song library listing 1602 through which users can select one or more songs (e.g., highlighted "Song C" in this example) and "add" it/them to the "Motivational Song Library" 1604 using the "Add" button icon 1606. Optionally, if necessary and desired, selection of the "Add" icon 1606 may activate systems, methods, and/or user interfaces to allow users to download and purchase the media content, e.g., from a remote, commercial, on-line source, etc. Songs may be removed from the Motivational Song Library 1604 using "Delete" icon 1608. Many variations in the content of, presentation of, and user interaction with a user interface for identifying and selecting motivational songs and controlling the content of a motivational song library are possible without departing from this invention. Also, while the discussion above (and much of that which follows) describes the motivational content in terms of "motivational songs," those skilled in the art will appreciate that motivational content may take on forms other than songs without departing from this invention, such as any desired audio, video, and/or media content; alphanumeric or textual content; e.g., that may be presented through a user carried portable playback device.

FIG. 16 illustrates another feature that may be available in systems and methods according to at least some examples of this invention. The user interface 1600 of this example requests users to select an "ultimate motivational song" (see area 1610). The ultimate motivational song may or may not be one of the songs included in the motivational song library 1604, and it may be used in a variety of ways. In this illustrated example, the ultimate motivational song may be changed by selection of the "change" button or icon 1612, and then selection of a different song (e.g., from the general listing 1602 or the motivational song library 1604) or vice versa. Other ways of selecting and changing the ultimate motivational song, when present, may be used without departing from this invention.

As noted above, the "ultimate motivational song" potentially may be used in a variety of ways in systems and methods according to examples of this invention. For example, if the "ultimate motivational song" is one of a user's favorite workout songs, its designation as the "ultimate motivational song" may cause it to be used more frequently by systems and methods according to some examples of the invention as opposed to other identified "motivational songs." In such situations and arrangements, the user will hear their favorite song more frequently, but because of the presence of other motivational songs in the library 1604, the ultimate motivational song will not be played in every instance that a motivational song is presented. As another example, the "ultimate motivational song" may be reserved for "special" workout occasions, e.g., when user goals or milestones are potentially within reach, when personal bests can be exceeded, etc., while other motivational songs may be used at other times, such as when a boost is needed, when the user falls below a pre-set pace, etc. As still another example, if desired, the ultimate motivational song may be reserved for use in response to user input requesting the motivational song (e.g., when button or icon 1506 is selected, as described in conjunction with FIG. 15), while the other motivational songs in the library 1604 may be automatically (optionally randomly) selected by systems and methods according to the invention, e.g., in response to (and/or in an effort to enhance) the user's performance. Systems and methods according to examples of this invention may use the ultimate motivational song (if any) in still other ways without departing from the invention.

Optionally, if desired, the motivational song library may be omitted in systems and methods according to some examples of this invention. If desired, a single motivational song may be identified by users (rather than a collection of songs), e.g., to provide motivational and/or reward content.

Figure 17:
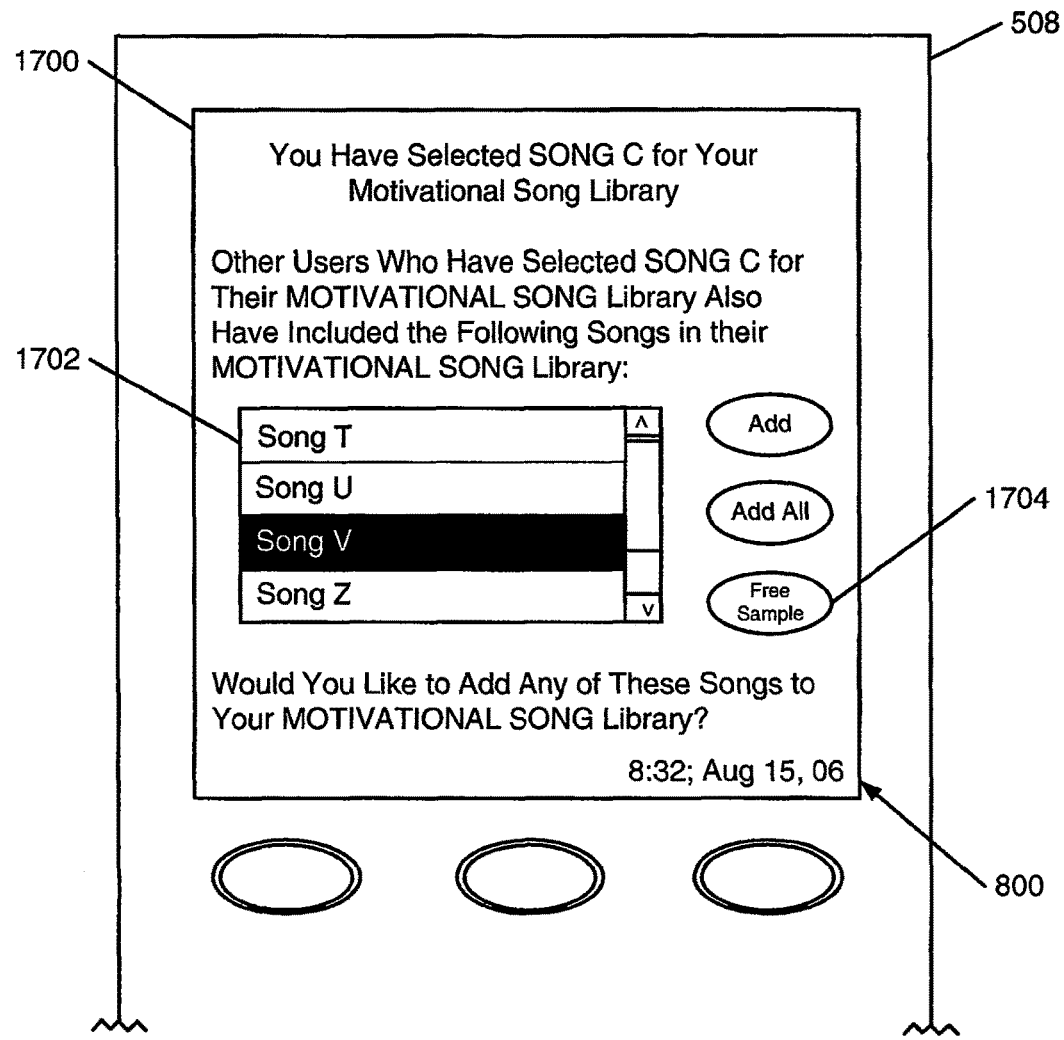

Systems and methods according to at least some examples of this invention may provide additional features relating to motivational songs and/or motivational song libraries. As described above, systems and methods according to at least some examples of this invention may connect to a remote system (e.g., system 704 from FIG. 7), for example, over the internet or another networked connection. Because the remote system also may receive data from other users, systems and methods according to examples of this invention may suggest or recommend media content to one user (e.g., motivational song content) based on motivational song information supplied by other users. For example, upon selection of a motivational song for one's motivation song library (as shown in FIG. 16), systems and methods according to at least some examples of this invention may provide suggestions or recommendations for additional motivational songs for the user's library. FIG. 17 illustrates one example of a user interface 1700 for performing this function. As shown in FIG. 17, upon selection of a specific song for the user's motivational song library, systems and methods according to this example of the invention may review the selection history of that song and/or the motivational song libraries of other users of the system (e.g., using remote system 704) and provide a listing 1702 of other suggested motivational songs based on the motivational song libraries of other users that have selected the same song for their motivational song library. Once the listing 1702 has been generated and presented to the user, the user may select one or more of the songs from the listing 1702 for inclusion in their own motivational song library. If necessary, appropriate interfaces may be provided to enable users to download and/or purchase any of the desired songs, e.g., from commercial and/or on-line sources. The "Free Sample" icon 1704 allows users to experience at least some portion(s) of a suggested song or media content, such as a movie clip (e.g., if they do not recognize the content), to provide additional information on which to base their selection decision.

Suggestions for additional songs (including motivational songs) or other media content are not limited to suggestions based on a specific song (or other content) selected by a user, and they are not limited to suggestions based on selections made by other users that have used the same song (or content). Based on the overall content of a user's song library, favorites listing, most played listing, motivational song library, etc., systems and methods according to at least some examples of this invention may suggest additional songs based on other factors, such as: songs from the same artist or groups as the songs included in one or more of the user's libraries or listings; songs of the same genre as the songs included in one or more of the user's libraries or listings; songs having the same or similar beat or cadence as the songs included in the user's libraries or listings; etc. Other similarity factors also may play a role in making these suggestions, such as similarities in age, gender, hobby listings, etc. Appropriate interfaces may be provided, e.g., like those described above in conjunction with FIG. 17, to display listings or titles of suggested songs to the user; to enable users to download and/or purchase any of the desired songs, e.g., from commercial and/or on-line sources, if necessary; to allow user "sampling;" etc.

Figure 18:
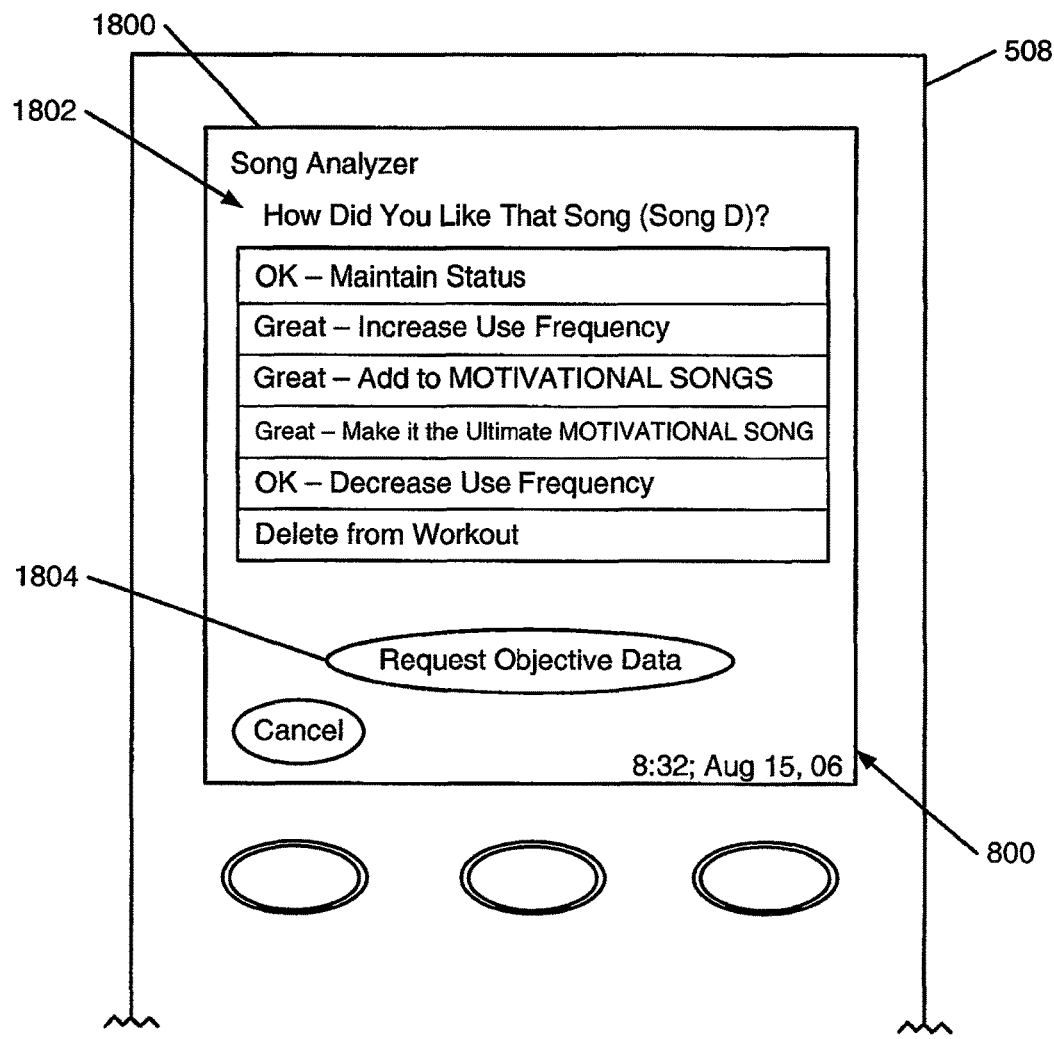

Subjective data, input by users, also may be used in systems and methods according to at least some examples of this invention, e.g., to at least in part control use and/or status of the media content (e.g., songs, videos, etc.). FIG. 18 illustrates one example. As a workout progresses and presentation of a song (or other media content) is completed, systems and methods according to at least some examples of this invention may request subjective user feedback relating to the song or other content. As shown in FIG. 18, the user interface 1800 of this example includes an area 1802 requesting that the user indicate how much they liked the previous content. In this illustrated example, the user may provide six potential responses to this inquiry, namely: (a) maintain the song at its current status (e.g., in its current play lists, at the same play frequency, etc.); (b) increase its play frequency; (c) add to "motivational songs library" (e.g., a motivational song as described above); (d) make it the "ultimate motivational song" (e.g., the ultimate motivational song as described above); (e) decrease its play frequency; and (f) remove it from the workout. Of course, these are just examples of potential options that may be included in area

1802. If desired, without departing from this invention, additional options may be included, one or more of the listed options may be omitted, other ways of presenting the options may be provided, etc.

FIG. 18 illustrates another feature that may be made available in systems and methods according to at least some examples of this invention. As described above, systems and methods according to at least some examples of this invention may include an electronic module 502 and/or other devices for sensing, tracking, and/or storing characteristics of the user's athletic performance (e.g., a speed and/or distance monitoring system, a cadence detecting or monitoring system, a physical or physiological parameter measuring system, etc.). The objective data relating to the user's athletic performance may be tracked with respect to the music or other media content presented to the user via electronic device 508 during the workout. In this manner, the objective effect of the media content on the user's athletic performance (if any) may be tracked, and the user can make decisions about the status of specific media content (e.g., its inclusion in a play list, its play frequency, its status as a motivational song, its status as the ultimate motivational song, etc.) based, at least in part, on objective data correlating the presentation of the content and the user's actual performance. In other words, systems and methods according to at least some examples of this invention may be used to identify songs and/or other media content that positively or negatively affect the user's athletic performance, optionally with respect to different activity types (e.g., while running, while using an elliptical machine, during weight lifting, etc.).

As more specific examples, for at least some users, presenting content having a beat (e.g., music beat or tempo) that closely corresponds to or matches the user's cadence during the workout activity (e.g., step landing during running, cycling or elliptical training machine foot presses or push-offs, rowing pulls, etc., for example, two music beats per step or exertion, or the like) can positively affect the user's performance. In other words, some users may consciously or subconsciously try to keep their steps or other exertion cadence in time with the music beat. This action may help these users maintain an increased pace for a longer time period (i.e., they may try to maintain cadence in time with the music, even as they tire and would normally slow down). The opposite effect also is possible (e.g., users may slow their step or exertion pace or cadence when music content having a slower beat is presented). Accordingly, systems and methods according to at least some examples of this invention (e.g., systems and methods that can correlate user performance characteristics with audio/video content presentation) also can be used to identify music and other content for users that may enhance and/or has been demonstrated as enhancing their performance. Additionally, by using data relating to music or other content having a positive effect on user performance, systems and methods according to this example of the invention may identify other content having similar characteristics (e.g., similar genre, beat, etc.), and the systems and methods may automatically suggest or present this content (e.g., songs) to the user. As yet additional examples, if desired, systems and methods according to at least some examples of this invention may alter the playback characteristics of music or other content to better match the characteristics of content demonstrated as having positively impacted the user's performance (e.g., speed up and/or slow down the music beat or playback of the music or other content to better match the beat of other positively impacting content, to better match user cadence or step pace, and/or to help alter user cadence, etc.).

Figure 19:
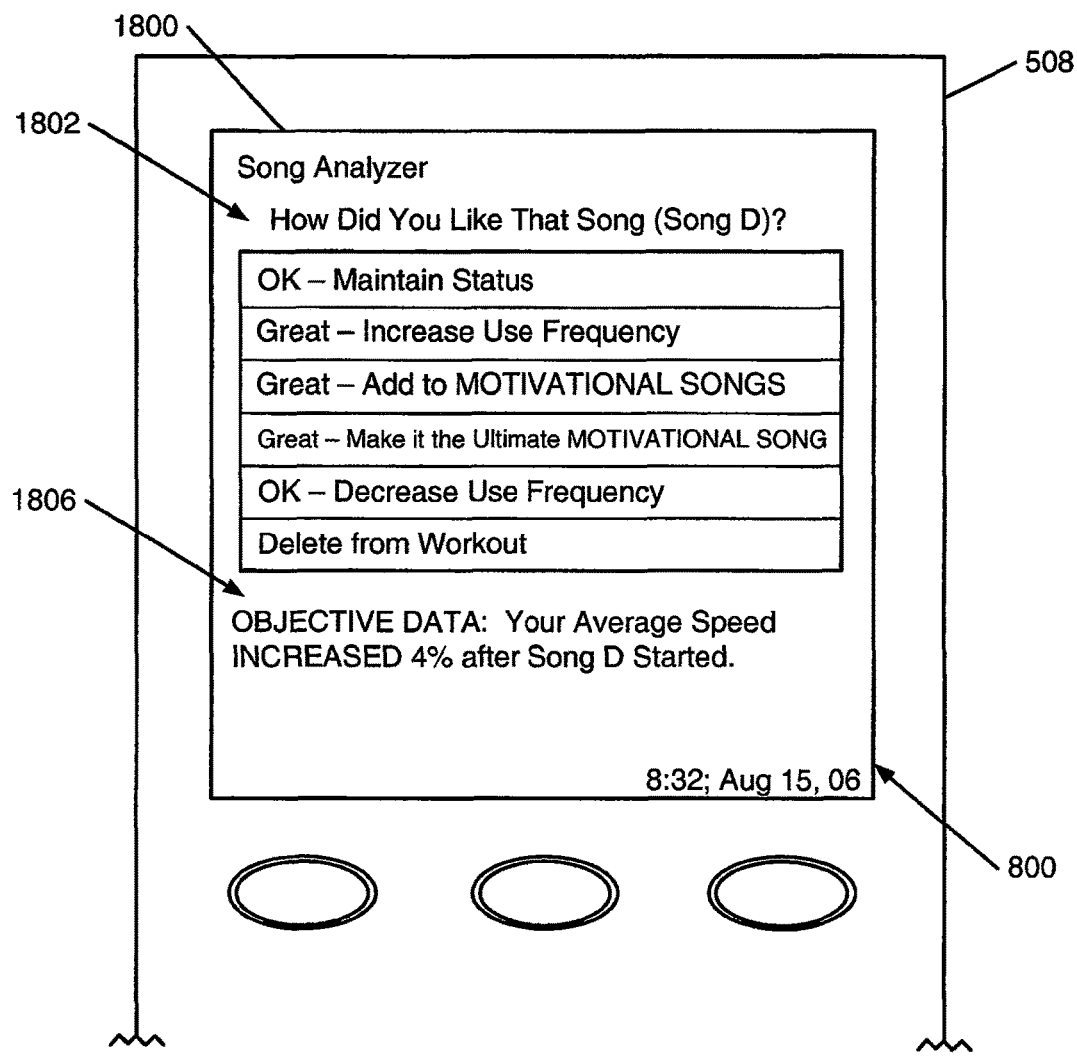

As shown in FIG. 18, the user interface 1800 includes an icon 1804 that allows users to request objective data relating to their performance during presentation of the identified song (or other media content). Selection of this icon 1804, in this illustrated example, changes the interface screen 1800, as shown in FIG. 19, to present objective data, if available, that relates to the user's athletic performance during presentation of the song (or other media content). In this illustrated example, area 1806 of the interface 1800 indicates performance change data (if any) that was sensed during presentation of the identified song (or other media content). If desired, the user can then make changes to the song's status, e.g., in area 1802, in the manner described above, based on this additional objective data. If desired, in at least some instances (e.g., when a strongly positive or negative performance impact is sensed), the objective data may be presented to the user automatically, without the need for user interaction or selection (e.g., using the interface 1800 and/or icon 1804, etc.).

Storing information relating to the objective impact of music or other media content on a user's athletic performance may be used in other ways by systems and methods according to at least some examples of this invention. For example, by identifying songs (or other media content) that appear to positively affect the user's performance, systems and methods according to at least some examples of this invention may be used to automatically present these songs at desired times during a workout (e.g., during an intense portion of a workout, when slowing is sensed, when predetermined goals or milestones are within reach, when a new personal best is within reach, etc.). In effect, using the objective performance data, systems and methods according to at least some examples of this invention can automatically generate a "motivational song library" and/or identify an "ultimate motivational song," as generally described above. Such automatically generated or identified content may be used in addition to and/or in place of the subjective and user identified libraries and/or content described above. Any desired conditions or parameters may be used in identifying a song or other media content for inclusion in the automatically generated "motivational song library" and/or "ultimate motivational song" (e.g., increased speed or other performance parameter by 1%, 2%, 3%, or more, etc.).

In addition to use of the objective data as correlated with media content output to provide an automatically generated "motivational song library" and/or "ultimate motivational song," the objective data may be used by systems and methods according to at least some examples of this invention, at least in part, to create entire workout routines for the user (including mixed music). For example, the objective data may be used to create workout routines including one or more activity types wherein music and/or other content is selected automatically for inclusion and presentation during the workout routines (e.g., in an effort to enhance the user's performance) based on the objective data indicating songs or other content that has positively impacted the user's performance (optionally on an activity type by activity type basis) in the past.

In addition to using objective data from one specific individual for inclusion in a proposed workout routine for that individual, objective data relating to certain media content and its effect on performance may be shared with others, for example, via the remote source 704, over the network (such as the internet), etc. As some more specific examples, workout routines or portions thereof from one user (including the media content) may be used by systems and methods according to the invention to create workout routines or portions thereof for one or more other users (including the media content) and/or to present certain media content (found to positively impact the performance of at least one user) to one or more other users at certain times. Optionally, systems and methods according to examples of the invention also may use the objective data and media content, at least in part, to present a workout routine (including media content) from one user to users having one or more of the same general characteristics as the user, such as similar height, weight, fitness level, workout lengths, activity types, combinations of activity types, the same gender, same hobbies, etc.

G. Miscellaneous Potential Features of Systems and Methods According to Examples of this Invention A wide variety of variations on the above-described features of systems, methods, and user interfaces therefor may be provided without departing from this invention, including variations on the user interface to include features commonly known and used in the art, e.g., features of commercially available computer and/or electronic device operating systems. While the following section describes certain potential and specific variations on features of systems, methods, and user interfaces therefor, those skilled in the art will recognize that other variations on these features and/or use or inclusion of other features are possible without departing from this invention. The following description of these specific features should not be construed as limiting or requiring systems, methods, and user interfaces according to the invention to include these specific features and/or as indicating that systems, methods, and user interfaces in accordance with this invention may not include additional or different features.

1. Reward Programs and/or Enhanced Feature Sets for Certain Users

Systems and methods according to at least some examples of this invention are not limited to situations and/or arrangements in which an electronic module (e.g., module 502, a pedometer type speed and/or distance measuring electronic module, a physical and/or physiological parameter measuring module, etc.) is included as part of or mounted in a receptacle provided in an article of footwear. Rather, the electronic module may be included in a variety of different products, such as in apparel (e.g., a shirt or jersey, as shown in FIG. 1); provided as a separate element carried or worn by the user; attached to the user's body, clothing, shoes, equipment, etc. (such as the wrist band element or the adhesively applied module shown in FIG. 1); etc. Any desired manner of mounting or carrying the electronic module may be used in accordance with at least some examples of this invention.

Even for modules that may be mounted and effectively used at various different locations or positions on a user's body or the like, systems and methods according to at least some examples of this invention may provide different functionality to the module and/or the overall athletic performance sensing and/or tracking system based on the manner in which the module is mounted, the equipment to which it is mounted, the manner in which it is used, the items or arrangement with which it was purchased or obtained, etc. As examples, if desired, users of systems and methods according to at least some examples of this invention may receive various "rewards" and/or "enhanced feature sets" when the modules are purchased and/or used with equipment provided by a certain manufacturer (e.g., purchased, mounted, and/or used in a predetermined manufacturer's clothing, footwear, and/or other equipment, etc.).

Any desired way of providing and/or activating the "reward" and/or "enhanced feature set" may be provided without departing from this invention. For example, the clothing, footwear, and/or other equipment for use with the module may include at least some portion of an activation and/or authentication system that interacts with the electronic module in some manner to provide and/or trigger availability of the "reward" and/or "enhanced feature set." Examples of such activation and/or authentication systems are described, for example, in U.S. patent application Ser. No. 11/166,351 filed Jun. 27, 2005, U.S. patent application Ser. No. 11/407,328 filed Apr. 20, 2006, and U.S. patent application Ser. No. 11/416,458 filed May 3, 2006. Each of these patent applications is entirely incorporated herein by reference. As another example, if desired, when a user purchases a module "enabled" or "ready" article of clothing, article of footwear, and/or piece of athletic equipment, they may be given coupons, an internet code, password, other access code, or other information that directly provide, activate, and/or provide access to the "reward" or "enhanced feature set." Other ways of activating and/or obtaining a "reward" and/or "enhanced feature set" and/or authenticating use of the electronic module with a particular article of clothing, article of footwear, and/or piece of athletic equipment may be used without departing from this invention.

The "reward" and/or "enhanced feature set" also may take on any desired form without departing from this invention. For example, as noted above, the "reward" may constitute a coupon (paper or electronic) for free or discounted merchandise (e.g., discount off future purchases, discount on the electronic module (or other equipment) when purchased with footwear, clothing, or equipment from a participating manufacturer, etc.); rebate offers; free additional merchandise with purchase of the module and footwear, clothing, or equipment from a participating manufacturer; etc. As additional examples, if desired, the remote system (e.g., system 704 in FIG. 7, such as a website, server, etc.) or other system for receiving, storing, processing, and/or managing the athletic performance data (e.g., run on or through computer 702 in FIG. 7) may provide enhanced functionality for module users who also have purchased footwear, clothing, or equipment from a participating manufacturer (e.g., longer term storage of data, additional interface features, additional data processing and/or display features, etc.). As yet further examples, if desired, the "reward" or "enhanced feature set" may constitute free access to a website or other computer program (optionally a limited time free access or introductory period) for storing and processing the athletic performance data for module users who also have purchased footwear, clothing, or equipment from a participating manufacturer (while module users who have not purchased footwear, clothing, or equipment from a participating manufacturer would be required to pay a fee or a higher fee for access to the website or computer program, optionally a monthly or other subscription type fee, etc.). A wide variety of other types of "rewards" and/or "enhanced feature sets" are possible without departing from this invention.

2. Athletic Performance Data Presentation

As is known, conventional athletic performance and exercise equipment is capable of presenting data and information to users regarding their performances or workouts (e.g., distance, time, speed, calories burned, metabolic equivalents ("METs"), etc.). Systems and methods according to at least some examples of this invention may be programmed and adapted to provide performance data and/or information to users in other forms or formats, e.g., so as to be more entertaining, motivational, goal-oriented, etc. For example, as for distance, rather than merely indicating miles or kilometers traveled, the distance data (e.g., distance traveled for a given workout, distance traveled over the course of two or more workouts, total distance traveled, etc.) may be presented as an indication of the distance traveled in the "real world." As more specific examples, the distance traveled data may be presented as a map of a relevant area (e.g., a user's local area, a state map, a U.S. map, a world map, etc.) showing the distance traveled by the user on the map. Such a presentation tool can help provide motivation and/or help users better define and visualize goals. For example, a user may have a "goal" of running on a treadmill or riding a stationary bicycle a distance "across their home state" within a specific time period (e.g., a month) or "across the U.S." within a specific time period (e.g., a year). Presenting such user's progress on a map can help them easily visualize their goals and current progress and/or provide motivation to continue working toward the goal in the future. Multiple users, optionally users involved in a virtual race, competing with one another, and/or striving to achieve a common goal, may be shown on a single map, e.g., for further motivational purposes.

The user's progress and/or goal may be presented on a map of any desired area without departing from this invention (e.g., a locally relevant map, a map of an area familiar to and/or selected by the user, etc.). Additionally or alternatively, the map may be changed over time, optionally automatically by systems and/or methods according to this invention. For example, for users with long distance running or biking goals, the displayed map may change as certain milestones are approached and/or achieved. For example, progress for a treadmill or exercise bicycle user having a goal of running or biking "across the U.S." may be displayed in various ways as the user's distance accumulates over time. During a workout in which the user's accumulated distance passes or approaches 350 miles, systems and methods according to at least some examples of this invention may display a map including San Diego, Calif. and Phoenix, Ariz. and advise the user, for example, as follows: "Congratulations. Today you passed the 350 mile mark toward your goal. As shown in this map, had you begun running in San Diego, you would have reached Phoenix today!" At a later time, this same user may reach the 700 mile mark. On that day, systems and methods according to this example of the invention may display a map including Washington, D.C. and Chicago, Ill. and advise the user, for example, as follows: "Congratulations. Today you passed the 700 mile mark toward your goal. As shown in this map, this is equivalent to the distance between Washington D.C. and Chicago, Ill. Keep up the good work!" Of course, a wide variety of messages, maps, starting/ending locations, and the like may be used without departing from this invention, and user input may be provided, at least in part, to indicate or define these features.

"Real world" goals for other workout activity types may include, for example: a total weight lifted goal (e.g., pounds.times.# of sets.times.# of repetitions/set, etc.) sufficient to lift the Brooklyn Bridge; total number of floors or hill incline climbed goal sufficient to climb Mt. Everest; total number of miles rowed goal sufficient to row across Lake Michigan; total miles skied goal sufficient to ski to the North Pole; etc. Any desired "real world" goals may be presented visually or in other manners in an effort to entertain and motivate users and to keep them interested in continuing their workout routines over time.

Other measured workout parameters also may be usefully expressed in "real world" terms, e.g., for entertainment, motivational, and/or goal-driven purposes. As further examples, information relating to workout intensity data (e.g., such as calories burned, METs, etc.) may be presented or displayed in more "real world" forms or formats. As more specific examples, "calorie" data and information may be presented (e.g., before a workout as a goal, during a workout, and/or in a post-workout analysis) in real world terms as being equivalent to certain foods or beverages. Of course, the display may present any desired food or beverages to the user without departing from this invention. As examples, if a user selects a "calorie burn" goal before beginning a workout, systems and methods according to examples of this invention may display icons or pictures of food or drink corresponding to the calorie burn goal (e.g., three hamburgers, two glasses of wine, a complete meal, etc., displayed, for example, on the exercise equipment display, on the portable electronic device 508, etc.). Then, as the workout progresses, these icons or pictures could disappear and/or change in appearance to indicate the extent to which the workout has been completed. Any desired way of presenting and/or changing the pictures or icons may be used without departing from this invention, such as: changing the color of the icon or picture (optionally in portions as the workout progresses); causing an increasing portion of the icon or picture to fade, gray, or disappear, etc.; causing an increasing portion of the icon or picture to colorize or appear; "X"-ing out the icon or picture (e.g., slowly superimposing an "X," "No" symbol, or similar character or icon over the food or drink icon or picture, etc.); etc. Additionally or alternatively, calorie burn data and information after the workout (or at other times) may be displayed (e.g., on the exercise equipment, on the electronic device 508, on a post-workout analysis computer (such as computer 702 in FIG. 7), etc.) as the equivalent food, drink, and/or meal pictures or icons.

3. Special or Targeted Workout Goals

As described above, systems and methods according to at least some examples of this invention may be used to provide pre-programmed workouts for users (optionally, user designed workout routines, third party designed workout routines, purchased workouts, downloaded workouts, combinations thereof, etc.). Such workouts may include a variety of different activity types, and optionally activities that change from workout-to-workout (e.g., different types of activities on different days, different workout parameters on different days, etc.).

Systems and methods according to some examples of this invention, may allow users to define their workouts and/or goals in other ways as well. For example, users may state their goals in more "real world" terms, such as: a "prewedding" (or pre-prom, pre-class reunion, or other event) weight loss workout program; a "swimsuit" workout program; a "flabby arm management" workout program; a "blood-pressure reduction" workout program; a "cholesterol control" workout program; etc. Given these "real world goals," optionally in combination with other data relating to the user or the goal (e.g., gender, height, weight, current fitness level, workout history, date of event, etc.), systems and methods according to at least some examples of this invention may provide a workout program designed to help the user better achieve the desired goal (optionally, receiving input from professionals).

The workout programs may be designed by third parties (e.g., coach, nutritionist, trainer, physician, etc.), optionally specially designed for the specific requesting individual, or they may be automatically selected by systems and methods according to the invention from previously designed and stored workout programs available to users. The workout routine for any individual day may be downloaded, for example, from another source (e.g., remote computer 704 or local computer 702 in FIG. 7, from a disk or other memory device, etc.) to the electronic device 508, electronic module 502, interface device 506, etc., which optionally may be used to control exercise equipment and/or other aspects of the workout, as described above.

4. Other Data or Information Presentation Techniques

User movement or activity when working out or participating in an athletic event or performance may make it difficult, in at least some instances (e.g., during particularly intensive portions of the workout or event, etc.), to read detailed information provided on a screen 800 of a small electronic device 508 (e.g., particularly if the information is presented in small fonts, etc.). Systems and methods according to at least some examples of this invention may be designed to provide at least some information to users in a quickly identifiable manner, e.g., in a manner that will not require reading small print.

One way of providing information to users in a quickly identifiable manner relates to the background color present on the display screen 800. For example, if desired, systems and methods according to at least some examples of this invention may make certain background colors correspond to a physical or physiological parameter associated with the workout. As more specific examples, the background color may be correlated to physical or physiological parameters such as current heart rate, total calories burned, total distance traveled, current pace, percentage of workout completed, etc. While any desired correlation between the background color and the physical or physiological parameter may be used without departing from this invention, in some examples of this invention the color may change over the visible spectrum (e.g., purple (for light/resting/beginning physical or physiological parameters, such as resting heart rate) changing to red (for heavy/intense/ending physical or physiological parameters, such as heart rate approaching a dangerous or desired maximum level), optionally with intermediate changes through one or more of blue, green, yellow, orange, etc. to indicate intermediate levels for the physical or physiological parameter(s). Of course, any numbers of colors, color combinations, color change schemes, and the like (including gray-scaling, cross-hatching or shading, line or font types/characteristics, etc.) may be used without departing from this invention. The color coding key (e.g., which colors are used and the manner in which they correlate to the levels of the physical or physiological parameters) may be user selected; pre-set by the system and/or method; determined based, at least part, on the user's personal characteristics (e.g., age, gender, height, weight, fitness level, history, etc.); and/or set in any other desired manner and/or using any other desired information.

The entire background of the screen 800 need not be changed or color coded to take advantage of these example aspects of the invention. As another example, if desired, a border of the screen 800 may include these types of color change and/or color coding features (more than one border may be provided or more than one color coded parameter may be provided using a single (potentially multi-colored) border, if desired, to provide information for more than one parameter). As another example, a portion of the screen (e.g., an "intensity block" in the upper left corner, etc.) may be provided to include one or more of these types of color change and/or color coding features. As yet additional examples, the desired physical or physiological data may be presented graphically or pictorially, such as by a bar graph, a "progress" chart (e.g., like those used to show download time remaining in commercially available computer operating systems), an analog type display (e.g., an analog speedometer or tachometer type display, etc.), a bouncing ball or other icon element (e.g., similar to graphic elements provided in conventional sound equalizer devices and/or applications), etc. As yet another example, font color (rather than background color) may be changed (e.g., using the color schemes described above) to quickly and easily provide information to users, e.g., of the types described above.

5. Fitness/Workout/Intensity Indices

Systems and methods according to at least some examples of this invention may allow users, equipment manufacturers, coaches, trainers, or others to design their own parameters or indices for tracking one's fitness, workout difficulty, workout intensity, and/or other workout characteristics. Any desired data and/or information may be used to formulate these indices, such as: age; gender; height; weight; workout intensity data (e.g., speed, set resistance levels, set incline levels, number of sets, number of repetitions, etc.); workout time/duration; elapsed time; elapsed distance; user's workout history; calorie burn; METs; etc. Any desired mathematical formula, algorithm, or scheme for combining information relating to one or more of these data items may be used without departing from this invention to arrive at a desired "index" to measure, track, and/or compare the fitness and/or workout characteristics of one or more individuals.

III. Conclusion

While the invention has been described with respect to specific examples including presently preferred modes of carrying out the invention, those skilled in the art will appreciate that there are numerous variations and permutations of the above described systems and methods. For example various aspects of the invention may be used in different combinations and various different subcombinations of aspects of the invention may be used together in a single system or method without departing from the invention. Also, various elements, components, and/or steps described above may be changed, changed in order, omitted, and/or additional elements, components, and/or steps may be added without departing from this invention. Additionally, while specific user interface elements and formats are shown in the illustrated examples, those skilled in the art will understand that any desired manner of presenting information to users and/or receiving their input may be used without departing from this invention. Also, while much of the above description relates to user interfaces provided on a portable electronic device that may be carried by the user during the performance (e.g., device 508), this is not a requirement. Alternatively or additionally, if desired, any of the features of the systems, methods, and/or user interfaces described above may be accessed, operated, and/or controlled through other computers, such as a personal computer (e.g., PC 702), the exercise equipment display screen or input panel, a remote computer (e.g., a gym's central computer, a networked computer, etc.), etc. Thus, the invention should be construed broadly as set forth in the appended claims.

What is claimed is:

1. A method comprising:
   storing, within a memory, a first plurality of motivational songs of a first motivational song library associated with a first device of a first user;
   communicating with a second device to identify a plurality of motivational song libraries that include at least one of the first plurality of motivational songs;

receiving a second plurality of motivational songs from the second device, wherein the second plurality of motivational songs include all of the motivational songs within the plurality of motivational song libraries that are not included in the first motivational song library;

filtering, at a processor associated with the first device, the second plurality of motivational songs based on a characteristic;

displaying the filtered second plurality of motivational songs on a display associated with the first device; and receiving an indication that the first user desires to add at least one song from the filtered second plurality of motivational songs to the first motivational song library.

2. The method of claim 1, wherein the communicating with the second device occurs when the first user is nearing a personal best in a particular activity metric.

3. The method of claim 1, wherein the communicating with the second device occurs when the first user has fallen behind a predetermined pace.

4. The method of claim 1, wherein the communicating with the second device occurs when the first user has reached a predetermined distance or location.

5. The method of claim 1, wherein at least one song in the first plurality of motivational songs comprises an ultimate motivational song.

6. The method of claim 1, further comprising: adding the at least one song from the filtered second plurality of motivational songs to the first motivational song library.

7. The method of claim 1, wherein the characteristic comprises at least one of a genre and cadence of each of the second plurality of motivational songs.

* * * * *